US012611555B2

(12) United States Patent
Zachs et al.

(10) Patent No.: US 12,611,555 B2
(45) Date of Patent: Apr. 28, 2026

(54) SYSTEMS AND METHODS FOR TARGETING AN ORGAN WITH ULTRASOUND STIMULATION FOR TREATING INFLAMMATION

(71) Applicant: SecondWave Systems, Inc., State College, PA (US)

(72) Inventors: Daniel P. Zachs, Minneapolis, MN (US); Anuj Bhardwaj, Minneapolis, MN (US); Jeffrey Heyman, Somerville, MA (US); Kashyap Patel, Hoboken, NJ (US); Claire Kaiser, Lake Forest Park, WA (US); John Basile, Minneapolis, MN (US); Hubert Hyoungil Lim, Saint Paul, MN (US); Gerardo Rodriguez Orellana, State College, PA (US)

(73) Assignee: SECONDWAVE SYSTEMS, INC., State College, PA (US)

( * ) Notice: Subject to any disclaimer, the term of this patent is extended or adjusted under 35 U.S.C. 154(b) by 49 days.

(21) Appl. No.: 18/015,256

(22) PCT Filed: Jul. 12, 2021

(86) PCT No.: PCT/US2021/041221
§ 371 (c)(1),
(2) Date: Jan. 9, 2023

(87) PCT Pub. No.: WO2022/011327
PCT Pub. Date: Jan. 13, 2022

(65) Prior Publication Data
US 2023/0264049 A1 Aug. 24, 2023

Related U.S. Application Data

(60) Provisional application No. 63/050,383, filed on Jul. 10, 2020.

(51) Int. Cl.
A61N 7/00 (2006.01)
A61B 8/00 (2006.01)
A61B 8/08 (2006.01)

(52) U.S. Cl.
CPC ............... *A61N 7/00* (2013.01); *A61B 8/085* (2013.01); *A61B 8/4427* (2013.01); *A61B 8/485* (2013.01);
(Continued)

(58) Field of Classification Search
CPC .................................................... A61B 5/4887
See application file for complete search history.

(56) References Cited

U.S. PATENT DOCUMENTS

| | | | |
|---|---|---|---|
| 3,550,586 A | 12/1970 | Balamuth | |
| 3,828,769 A | 8/1974 | Mettler | |
| 4,617,931 A | 10/1986 | Dory | |
| 4,787,394 A | 11/1988 | Ogura | |
| 4,883,045 A | 11/1989 | Theisz | |
| 4,958,626 A | 9/1990 | Nambu et al. | |

(Continued)

FOREIGN PATENT DOCUMENTS

| | | |
|---|---|---|
| CN | 87217195 | 11/1988 |
| CN | 1185982 A | 7/1998 |

(Continued)

OTHER PUBLICATIONS

Pashaei et al., Flexible Body-Conformal Ultrasound Patches for Image-Guided Neuromodulation, IEEE Transactions on Biomedical Circuits and Systems, 2020, 14(2):305-318.
(Continued)

*Primary Examiner* — Nyrobi Celestine
(74) *Attorney, Agent, or Firm* — QUARLES & BRADY LLP

(57) ABSTRACT

A method for directing ultrasound energy toward an organ of a subject, including: determining a location of the organ within the subject's body; and directing ultrasound energy at
(Continued)

1100 the location of the organ within the subject's body using a wearable ultrasound device.

19 Claims, 27 Drawing Sheets

(52) U.S. Cl.
CPC ................. *A61N 2007/0004* (2013.01); *A61N 2007/0052* (2013.01)

(56) References Cited

U.S. PATENT DOCUMENTS

| | | | |
|---|---|---|---|
| 5,018,508 | A | 5/1991 | Fry et al. |
| 5,172,692 | A | 12/1992 | Kulow et al. |
| 5,471,988 | A | 12/1995 | Fujio et al. |
| 5,476,438 | A | 12/1995 | Edrich et al. |
| 5,523,058 | A | 6/1996 | Umemura et al. |
| 5,524,624 | A | 6/1996 | Tepper et al. |
| 5,558,092 | A | 9/1996 | Unger et al. |
| 5,601,526 | A | 2/1997 | Chapelon et al. |
| 5,620,409 | A | 4/1997 | Venuto et al. |
| 5,722,411 | A | 3/1998 | Suzuki et al. |
| 5,807,285 | A | 9/1998 | Vaitekunas et al. |
| 5,836,896 | A | 11/1998 | Rosenschein |
| 5,873,828 | A | 2/1999 | Fujio et al. |
| 5,895,348 | A | 4/1999 | Hosaka |
| 5,904,659 | A | 5/1999 | Duarte et al. |
| 6,066,123 | A | 5/2000 | Li et al. |
| 6,068,596 | A | 5/2000 | Weth et al. |
| 6,071,494 | A | 6/2000 | Unger |
| 6,206,843 | B1 | 3/2001 | Iger et al. |
| 6,371,903 | B1 | 4/2002 | Blanc et al. |
| 6,381,483 | B1 | 4/2002 | Hareyama et al. |
| 6,390,995 | B1 | 5/2002 | Ogden et al. |
| 6,413,216 | B1 | 7/2002 | Cain et al. |
| 6,450,979 | B1 | 9/2002 | Miwa et al. |
| 6,488,639 | B1 | 12/2002 | Ribault et al. |
| 6,548,047 | B1 | 4/2003 | Unger |
| 6,576,875 | B1 | 6/2003 | Kleffner et al. |
| 6,599,256 | B1 | 7/2003 | Acker et al. |
| 6,607,502 | B1 | 8/2003 | Maguire et al. |
| 6,623,430 | B1 | 9/2003 | Slayton et al. |
| 6,635,054 | B2 | 10/2003 | Fjield et al. |
| 6,641,599 | B2 | 11/2003 | Peterson et al. |
| 6,733,450 | B1 | 5/2004 | Alexandrov et al. |
| 6,821,274 | B2 | 11/2004 | McHale et al. |
| 6,850,804 | B2 | 2/2005 | Eggers et al. |
| 8,725,251 | B2 | 5/2014 | Della Rocca et al. |
| 9,717,921 | B2 | 8/2017 | Perryman et al. |
| 10,556,132 | B2 | 2/2020 | Tyler |
| 11,235,178 | B2 | 2/2022 | Puleo et al. |
| 11,911,634 | B2 | 2/2024 | Puleo et al. |
| 2002/0188230 | A1 | 12/2002 | Savrasov et al. |
| 2003/0018256 | A1 | 1/2003 | Sasaki et al. |
| 2003/0078227 | A1 | 4/2003 | Greenleaf et al. |
| 2003/0152517 | A1 | 8/2003 | Peyman |
| 2003/0181890 | A1 | 9/2003 | Schulze et al. |
| 2004/0030227 | A1 | 2/2004 | Littrup et al. |
| 2004/0034304 | A1 | 2/2004 | Sumi |
| 2004/0073079 | A1 | 4/2004 | Altshuler et al. |
| 2004/0122493 | A1 | 6/2004 | Ishibashi et al. |
| 2004/0153009 | A1 | 8/2004 | Horzewski et al. |
| 2004/0187876 | A1 | 9/2004 | Myhr |
| 2004/0248832 | A1 | 12/2004 | Davidson |
| 2005/0000101 | A1 | 1/2005 | Forssmann |
| 2005/0000804 | A1 | 1/2005 | Oldenburg |
| 2005/0024021 | A1 | 2/2005 | Zeiler et al. |
| 2005/0240103 | A1* | 10/2005 | Byrd ................... G01S 7/52033 |
| | | | 600/437 |
| 2006/0002876 | A1 | 1/2006 | Cahen |
| 2006/0287678 | A1 | 12/2006 | Shafer |
| 2007/0167801 | A1* | 7/2007 | Webler .................... G06T 19/00 |
| | | | 600/459 |

| | | | |
|---|---|---|---|
| 2008/0146942 | A1* | 6/2008 | Dala-Krishna ...... A61B 8/4488 |
| | | | 600/466 |
| 2009/0005675 | A1* | 1/2009 | Grunwald ............. A61B 5/349 |
| | | | 600/467 |
| 2011/0152666 | A1 | 6/2011 | Shanbhag et al. |
| 2012/0127157 | A1* | 5/2012 | Adler ..................... G06Q 10/00 |
| | | | 345/419 |
| 2012/0130201 | A1* | 5/2012 | Jain .......................... A61B 5/08 |
| | | | 600/301 |
| 2014/0000582 | A1 | 1/2014 | Pelletier |
| 2014/0058292 | A1 | 2/2014 | Alford et al. |
| 2014/0288412 | A1 | 9/2014 | Schwartz |
| 2015/0011995 | A1* | 1/2015 | Avitall .............. A61B 18/1206 |
| | | | 606/46 |
| 2015/0151142 | A1* | 6/2015 | Tyler ........................ A61B 6/03 |
| | | | 601/2 |
| 2016/0136462 | A1 | 5/2016 | Lewis, Jr. et al. |
| 2017/0000078 | A1 | 1/2017 | Alford et al. |
| 2017/0007853 | A1 | 1/2017 | Alford et al. |
| 2017/0080255 | A1 | 3/2017 | Law et al. |
| 2017/0095670 | A1* | 4/2017 | Ghaffari ................ A61M 21/02 |
| 2017/0262982 | A1* | 9/2017 | Pagoulatos ........... G06V 10/82 |
| 2017/0360329 | A1* | 12/2017 | Derkx .................. A61B 5/7278 |
| 2019/0269942 | A1 | 9/2019 | Alford et al. |

FOREIGN PATENT DOCUMENTS

| | | | |
|---|---|---|---|
| CN | 1212897 | A | 4/1999 |
| CN | 1241445 | A | 1/2000 |
| CN | 1260217 | A | 7/2000 |
| CN | 2460061 | Y | 11/2001 |
| CN | 2503915 | Y | 8/2002 |
| CN | 2503916 | Y | 8/2002 |
| CN | 1372988 | A | 10/2002 |
| CN | 1463772 | A | 12/2003 |
| CN | 2742929 | Y | 11/2005 |
| CN | 104857643 | A | 8/2015 |
| CN | 108652669 | A | 10/2018 |
| CN | 1277064 | A | 12/2020 |
| DE | 3900433 | A1 | 7/1990 |
| DE | 4414239 | A1 | 10/1994 |
| DE | 102004004415 | A1 | 8/2005 |
| JP | 2016523163 | A | 8/2016 |
| JP | 2017108761 | A | 6/2017 |
| JP | 2019534090 | A | 11/2019 |
| RU | 2128067 | C1 | 3/1999 |
| WO | 1993017646 | A2 | 9/1993 |
| WO | 1997040679 | A1 | 11/1997 |
| WO | 1999025385 | A1 | 5/1999 |
| WO | 1999027991 | A1 | 6/1999 |
| WO | 1999037364 | A1 | 7/1999 |
| WO | 2000006032 | A1 | 2/2000 |
| WO | 2000007494 | A2 | 2/2000 |
| WO | 2000015097 | A3 | 3/2000 |
| WO | 2000027293 | A1 | 5/2000 |
| WO | 2000038602 | A1 | 7/2000 |
| WO | 2000069376 | A1 | 11/2000 |
| WO | 2000071207 | A1 | 11/2000 |
| WO | 2001089723 | A1 | 11/2001 |
| WO | 2002015768 | A2 | 2/2002 |
| WO | 2002043564 | A2 | 6/2002 |
| WO | 2003003929 | A1 | 1/2003 |
| WO | 2003013654 | A1 | 2/2003 |
| WO | 2003015862 | A2 | 2/2003 |
| WO | 2003039674 | A1 | 5/2003 |
| WO | 2003039675 | A1 | 5/2003 |
| WO | 2003077833 | A2 | 9/2003 |
| WO | 2003105676 | A2 | 12/2003 |
| WO | 2004016315 | A1 | 2/2004 |
| WO | 2004075977 | A2 | 9/2004 |
| WO | 2004103461 | A1 | 12/2004 |
| WO | 2005039526 | A1 | 5/2005 |
| WO | 2005092433 | A1 | 10/2005 |
| WO | 2014153223 | A1 | 9/2014 |
| WO | 2017138090 | A1 | 8/2017 |
| WO | 2018081826 | A1 | 5/2018 |

(56)                References Cited

FOREIGN PATENT DOCUMENTS

WO        2020150733  A1      7/2020
WO        2021188200  A2      9/2021
WO        2021222892  A1     11/2021

OTHER PUBLICATIONS

PCT International Search Report and Written Opinion, PCT/US2021/041221, Nov. 17, 2021, 17 pages.
European Patent Office, Extended European Search Report, Application No. 21838081.4, dated Jun. 6, 2024, 8 pages.
PCT International Preliminary Report on Patentability, PCT/US2021/041221, Jan. 10, 2023, 15 pages.
Japan Patent Office, First Office Action issued in corresponding Japanese Patent Application No. 2023-501620, dated Jan. 23, 2025 [4 pgs.].

Hoogland, Ultrasound therapy, Dec. 2025, Implox Healthcare, Enraf Nonius B.V. The Netherlands [43 pgs.].
Baker, et al., A Review of Therapeutic Ultrasound: Biophysical Effects, Physical Therapy, vol. 81, No. 7, Jul. 2001 [8 pgs.].
Terhaar, Therapeutic ultrasound, European Journal of Ultrasound 9, Elsevier Science Ireland Ltd., 1991, pp. 3-9 [9 pgs.]
Hynynen, et al., A Clinical, Noninvasive, MR Imaging-Monitored Ultrasound Surgery Method, Imaging & Therapeutic Technology, RadioGraphics 1996:16:185-195 [11 pgs.]
Maxwell, Therapeutic Ultrasound: Its Effects on the Cellular and Molecular Mechanisms of Inflammation and Repair, Physiotherapy, vol. 78, Issue. 6, Jun. 10, 1992, pp. 421-426 [6 pgs].
Saad, Therapeutic ultrasound and the liver in vivo: Action and possible mechanisms, Ultrasound in medicine & biology, 1986-11, vol. 12 (11) pp. 855-863 [9 pgs.]
Pashaei, et al., Flexible Body-Conformal Ultrasound Patches for Image-Guided Neuromodulation, IEEE Transactions on Biomedical Circuits and Systems, vol. 14, No. 2, Apr. 2000, CPA Global [14 pgs].

* cited by examiner

Figure 3: Splenic motion can be accurately measured by an accelerometer

Figure 6: Accelerometry recordings from five torso placements

Figure 7: Accelerometry can track breathing and spleen motion in different orientations Torso clipart from openclipart.org is released into the Public Domain for unlimited commercial use.

1100

1300

1302

DETERMINE A LOCATION OF THE ORGAN WITHIN THE SUBJECT'S BODY

1304

DIRECT ULTRASOUND ENERGY AT THE LOCATION OF THE ORGAN WITHIN THE SUBJECT'S BODY USING A WEARABLE ULTRASOUND DEVICE

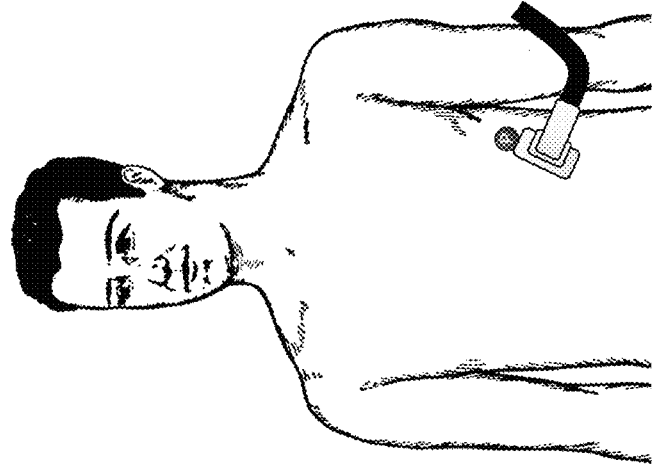
FIG. 14

SYSTEMS AND METHODS FOR TARGETING AN ORGAN WITH ULTRASOUND STIMULATION FOR TREATING INFLAMMATION

CROSS-REFERENCE TO RELATED APPLICATIONS

The present application is a U.S. national phase application of International Patent Application No. PCT/US2021/041221 filed on Jul. 12, 2021, which international patent application is based on and claims priority to U.S. Provisional Patent Application No. 63/050,383 filed on Jul. 10, 2020, the entire disclosure of both of which is incorporated herein by reference.

STATEMENT REGARDING FEDERALLY SPONSORED RESEARCH

This invention was made with government support under 140D0419C0092 awarded by the Defense Advanced Research Projects Agency. The government has certain rights in the invention.

BACKGROUND

Acute and chronic inflammatory conditions can be treated using pharmaceutical drugs, which systemically and indiscriminately reduce inflammation by blocking cytokines or suppressing the immune system. These anti-inflammatory agents may be used to treat arthritis, psoriasis, inflammatory bowel disease, colitis, kidney disease, heart disease, and other inflammatory disorders. These anti-inflammatory agents can also be used to treat uncomfortable or even deadly symptoms associated with infections, such as those arising due to sepsis or viruses. However, some patients may not respond to primary treatment and may seek out several different pharmaceuticals or a combination of them to manage their illness. Furthermore, these drugs may be associated with a long list of mild to severe side-effects.

SUMMARY OF THE INVENTION

Accordingly, new systems, methods, and apparatuses for treating acute and chronic inflammatory conditions are desirable.

One aspect provides a method for directing ultrasound energy toward an organ of a subject, including: determining a location of the organ within the subject's body; and directing ultrasound energy at the location of the organ within the subject's body using a wearable ultrasound device.

In various aspects of the method, determining the location of the organ within the subject's body may include obtaining biosensor data from a biosensor associated with the subject's body, determining a correlation between the biosensor data and the location of the organ within the subject's body, and determining the location of the organ within the subject's body based on the correlation.

In some aspects of the method, obtaining biosensor data from a biosensor associated with the subject's body may include obtaining biosensor data from an accelerometer associated with the subject's body.

In other aspects of the method, determining a correlation between the biosensor data and the location of the organ within the subject's body may include determining the correlation between the biosensor data from the accelerometer and the location of the organ within the subject's body and determining the location of the organ within the subject's body based on the correlation.

In certain other aspects of the method, determining a correlation between the biosensor data and the location of the organ within the subject's body may include determining the correlation between the biosensor data and the location of the organ within the subject's body based on correlation data in a database.

In various aspects of the method, obtaining biosensor data from a biosensor associated with the subject's body may include obtaining biosensor data from at least one of a pulse oximeter, a respirometer, an EMG electrode, or an EKG electrode associated with the subject's body.

In some aspects of the method, determining the subject's body position based on the biosensor data may include determining, based on the biosensor data, whether the subject's body is standing, sitting, moving, or lying.

In certain aspects of the method, determining a location of the organ within the subject's body during movement of the organ may include obtaining the biosensor data from the biosensor associated with the subject's body, determining the subject's breathing status based on the biosensor data, and determining the location of the organ within the subject's body based on the subject's breathing status.

In some other aspects of the method, obtaining the biosensor data from the biosensor associated with the subject's body may include obtaining the biosensor data from a respirometer associated with the subject's body.

In other aspects of the method, determining the subject's breathing status based on the biosensor data may include determining, based on the biosensor data, whether the subject's breathing status is breathing quickly or breathing slowly.

In various aspects of the method, directing ultrasound energy at the location of the organ within the subject's body using a wearable ultrasound device may include directing ultrasound energy at the location of the organ within the subject's body using the wearable ultrasound device based on determining that the subject's body position is sitting and that the subject's breathing status is breathing slowly.

In some aspects of the method, directing ultrasound energy at the location of the organ within the subject's body using a wearable ultrasound device may include directing ultrasound energy at the location of the organ within the subject's body using the wearable ultrasound device for at least nine minutes.

In particular aspects of the method, obtaining biosensor data from a biosensor associated with the subject's body may include obtaining biosensor data from at least one of an accelerometer, a pulse oximeter, a respirometer, an EMG electrode, or an EKG electrode associated with the subject's body.

In some aspects of the method, determining the subject's body position based on the biosensor data may include determining, based on the biosensor data, whether the subject's body is standing, sitting, moving, or lying.

In some other aspects of the method, determining a location of the organ within the subject's body during movement of the organ may include obtaining the biosensor data from the biosensor associated with the subject's body, determining the subject's breathing status based on the biosensor data, and determining the location of the organ within the subject's body based on the subject's breathing status.

In certain aspects of the method, obtaining the biosensor data from the biosensor associated with the subject's body may include obtaining the biosensor data from a respirometer associated with the subject's body.

In various aspects of the method, determining the subject's breathing status based on the biosensor data may include determining, based on the biosensor data, whether the subject's breathing status is breathing quickly or breathing slowly.

In particular aspects of the method, directing ultrasound energy at the location of the organ within the subject's body using a wearable ultrasound device may include directing ultrasound energy at the location of the organ within the subject's body using the wearable ultrasound device based on determining that the subject's body position is sitting and that the subject's breathing status is breathing slowly.

In certain aspects of the method, directing ultrasound energy at the location of the organ within the subject's body using a wearable ultrasound device may include directing ultrasound energy at the location of the organ within the subject's body using the wearable ultrasound device for at least nine minutes.

In some aspects of the method, determining a location of the organ within the subject's body may include determining the location of the organ within the subject's body using a non-invasive imaging modality.

In other aspects of the method, determining the location of the organ within the subject's body using a non-invasive imaging modality may include non-invasively generating an image of the location of the organ within the subject's body using the wearable ultrasound device.

In particular aspects of the method, determining the location of the organ within the subject's body using the wearable ultrasound device may include detecting a location of a rib within the subject's body using the wearable ultrasound device, adjusting an output of the wearable ultrasound device to avoid the location of the rib within the subject's body, and directing ultrasound energy at the organ within the subject's body based on the adjusted output of the wearable ultrasound device.

In some aspects of the method, determining a location of the organ within the subject's body may include determining a location of the organ within the subject's body based on elastography measurements of the organ using the wearable device.

In certain aspects of the method, determining a location of the organ within the subject's body may include determining a location of the organ within the subject's body based on ultrasound-resolved border detection of the organ using the wearable device.

In particular aspects of the method, determining a location of the organ within the subject's body may include determining a location of the organ within the subject's body based on ultrasound detection of at least one of a blood vessel or a nerve associated with the organ using the wearable device.

In certain aspects of the method, determining the location of the organ within the subject's body may include determining, for each of a plurality of positions of the subject's body, the location of the organ within the subject's body using a non-invasive imaging modality, collecting, for each of the plurality of positions of the subject's body, initial biosensor data from at least one of the wearable ultrasound device, an accelerometer, a pulse oximeter, a respirometer, an EMG electrode, or an EKG electrode associated with the subject's body, and generating, for each of the plurality of positions of the subject's body, correlations of the location of the organ within the subject's body with the initial biosensor data.

In particular aspects of the method, determining the location of the organ within the subject's body may include storing the correlations of the location of the organ within the subject's body with the initial biosensor data in a database.

In some aspects of the method, determining a location of the organ within the subject's body during movement of the subject may include collecting additional biosensor data from at least one of the wearable ultrasound device, the accelerometer, the pulse oximeter, the respirometer, the EMG electrode, or the EKG electrode associated with the subject's body, determining the location of the organ within the subject's body based on the additional biosensor data and the correlations stored in the database, and directing ultrasound energy at the organ within the subject's body based on the determined location.

In various aspects of the method, the organ may be a spleen.

Another aspect provides a system for directing ultrasound energy toward an organ of a subject, including a wearable ultrasound device configured to: determine a location of the organ within the subject's body; and direct ultrasound energy at the location of the organ within the subject's body.

In various aspects of the system, the wearable ultrasound device, when determining the location of the organ within the subject's body may be further configured to obtain biosensor data from a biosensor associated with the subject's body, determine a correlation between the biosensor data and the location of the organ within the subject's body, and determine the location of the organ within the subject's body based on the correlation.

In some aspects of the system, the wearable ultrasound device, when obtaining biosensor data from a biosensor associated with the subject's body may be further configured to obtain biosensor data from an accelerometer associated with the subject's body.

In certain aspects of the system, the wearable ultrasound device, when determining a correlation between the biosensor data and the location of the organ within the subject's body may be further configured to determine the correlation between the biosensor data from the accelerometer and the location of the organ within the subject's body, and determine the location of the organ within the subject's body based on the correlation.

In particular aspects of the system, the wearable ultrasound device, when determining a correlation between the biosensor data and the location of the organ within the subject's body may be further configured to determine the correlation between the biosensor data and the location of the organ within the subject's body based on correlation data in a database.

In some aspects of the system, the wearable ultrasound device, when obtaining biosensor data from a biosensor associated with the subject's body may be further configured to obtain biosensor data from at least one of a pulse oximeter, a respirometer, an EMG electrode, or an EKG electrode associated with the subject's body.

In various aspects of the system, the wearable ultrasound device, when determining the subject's body position based on the biosensor data may be further configured to determine, based on the biosensor data, whether the subject's body is standing, sitting, moving, or lying.

In particular aspects of the system, the wearable ultrasound device, when determining a location of the organ within the subject's body during movement of the organ may be further configured to obtain the biosensor data from the biosensor associated with the subject's body, determine the subject's breathing status based on the biosensor data, and determine the location of the organ within the subject's body based on the subject's breathing status.

In some aspects of the system, the wearable ultrasound device, when obtaining the biosensor data from the biosensor associated with the subject's body may be further configured to obtain the biosensor data from a respirometer associated with the subject's body.

In certain aspects of the system, the wearable ultrasound device, when determining the subject's breathing status based on the biosensor data may be further configured to determine, based on the biosensor data, whether the subject's breathing status is breathing quickly or breathing slowly.

In particular aspects of the system, the wearable ultrasound device, when directing ultrasound energy at the location of the organ within the subject's body using a wearable ultrasound device may be further configured to direct ultrasound energy at the location of the organ within the subject's body using the wearable ultrasound device based on determining that the subject's body position is sitting and that the subject's breathing status is breathing slowly.

In various aspects of the system, the wearable ultrasound device, when directing ultrasound energy at the location of the organ within the subject's body using a wearable ultrasound device may be further configured to direct ultrasound energy at the location of the organ within the subject's body using the wearable ultrasound device for at least nine minutes.

In some aspects of the system, the wearable ultrasound device, when obtaining biosensor data from a biosensor associated with the subject's body may be further configured to obtain biosensor data from at least one of an accelerometer, a pulse oximeter, a respirometer, an EMG electrode, or an EKG electrode associated with the subject's body.

In certain aspects of the system, the wearable ultrasound device, when determining the subject's body position based on the biosensor data may be further configured to determine, based on the biosensor data, whether the subject's body is standing, sitting, moving, or lying.

In particular aspects of the system, the wearable ultrasound device, when determining a location of the organ within the subject's body during movement of the organ may be further configured to obtain the biosensor data from the biosensor associated with the subject's body, determine the subject's breathing status based on the biosensor data, and determine the location of the organ within the subject's body based on the subject's breathing status.

In some aspects of the system, the wearable ultrasound device, when obtaining the biosensor data from the biosensor associated with the subject's body may be further configured to obtain the biosensor data from a respirometer associated with the subject's body.

In certain aspects of the system, the wearable ultrasound device, when determining the subject's breathing status based on the biosensor data may be further configured to determine, based on the biosensor data, whether the subject's breathing status is breathing quickly or breathing slowly.

In particular aspects of the system, the wearable ultrasound device, when directing ultrasound energy at the location of the organ within the subject's body using a wearable ultrasound device may be further configured to direct ultrasound energy at the location of the organ within the subject's body using the wearable ultrasound device based on determining that the subject's body position is sitting and that the subject's breathing status is breathing slowly.

In certain aspects of the system, the wearable ultrasound device, when directing ultrasound energy at the location of the organ within the subject's body using a wearable ultrasound device may be further configured to direct ultrasound energy at the location of the organ within the subject's body using the wearable ultrasound device for at least nine minutes.

In some aspects of the system, the wearable ultrasound device, when determining a location of the organ within the subject's body may be further configured to determine the location of the organ within the subject's body using a non-invasive imaging modality.

In various aspects of the system, the wearable ultrasound device, when determining the location of the organ within the subject's body using a non-invasive imaging modality may be further configured to non-invasively generate an image of the location of the organ within the subject's body using the wearable ultrasound device.

In particular aspects of the system, the wearable ultrasound device, when determining the location of the organ within the subject's body using the wearable ultrasound device may be further configured to detect a location of a rib within the subject's body using the wearable ultrasound device, adjust an output of the wearable ultrasound device to avoid the location of the rib within the subject's body, and direct ultrasound energy at the organ within the subject's body based on the adjusted output of the wearable ultrasound device.

In certain aspects of the system, the wearable ultrasound device, when determining a location of the organ within the subject's body may be further configured to determine a location of the organ within the subject's body based on elastography measurements of the organ using the wearable device.

In some aspects of the system, the wearable ultrasound device, when determining a location of the organ within the subject's body may be further configured to determine a location of the organ within the subject's body based on ultrasound-resolved border detection of the organ using the wearable device.

In various aspects of the system, the wearable ultrasound device, when determining a location of the organ within the subject's body may be further configured to determine a location of the organ within the subject's body based on ultrasound detection of at least one of a blood vessel or a nerve associated with the organ using the wearable device.

In particular aspects of the system, the wearable ultrasound device, when determining the location of the organ within the subject's body may be further configured to determine, for each of a plurality of positions of the subject's body, the location of the organ within the subject's body using a non-invasive imaging modality, collect, for each of the plurality of positions of the subject's body, initial biosensor data from at least one of the wearable ultrasound device, an accelerometer, a pulse oximeter, a respirometer, an EMG electrode, or an EKG electrode associated with the subject's body, and generate, for each of the plurality of positions of the subject's body, correlations of the location of the organ within the subject's body with the initial biosensor data.

In various aspects of the system, the wearable ultrasound device, when determining the location of the organ within the subject's body may be further configured to store the correlations of the location of the organ within the subject's body with the initial biosensor data in a database.

In some aspects of the system, the wearable ultrasound device, when determining a location of the organ within the subject's body during movement of the subject may be further configured to collect additional biosensor data from at least one of the wearable ultrasound device, the accelerometer, the pulse oximeter, the respirometer, the EMG electrode, or the EKG electrode associated with the subject's body, determine the location of the organ within the subject's body based on the additional biosensor data and the correlations stored in the database, and direct ultrasound energy at the organ within the subject's body based on the determined location.

In various aspects of the system, the organ may be a spleen.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIG. 9A shows a perspective view of a wearable ultrasound device on a subject's chest; FIG. 9B shows a cross-sectional view of a subject's chest region depicting the locations of the spleen S, a rib R, and a wearable ultrasonic device W; FIG. 9C shows a diagram of the wearable device emitting ultrasonic energy towards a rib; FIG. 9D shows a diagram of ultrasonic energy being reflected back towards the wearable device; and FIG. 9E shows a diagram of the wearable device emitting ultrasonic energy towards the spleen after having made adjustments to the ultrasonic beam based on detection of the rib.

FIGS. 14-24 show examples of how the spleen location may be tracked and characterized in a subject using ultrasound imaging for a variety of body positions and breathing patterns of the subject.

DETAILED DESCRIPTION

Figure 1:
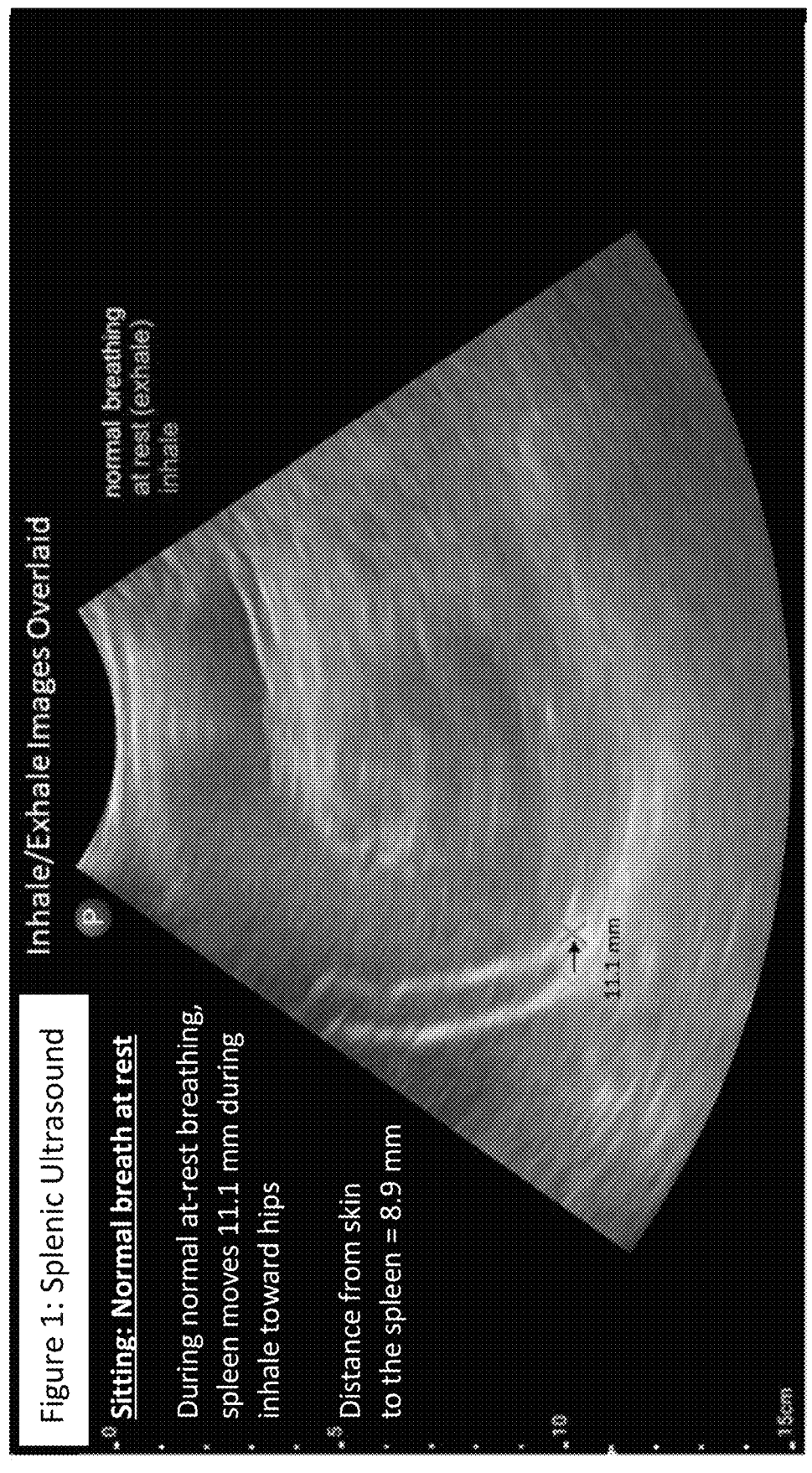
FIG. 1 shows a pair of overlaid ultrasound images of the spleen which show how the spleen moves during breathing.

In accordance with some embodiments of the disclosed subject matter, mechanisms (which can include systems, methods, and media) for directing ultrasound energy at an organ are provided.

There has been work in the field of bioelectronics medicine in which peripheral nerves (e.g., vagus nerve) and end-organs (i.e. organs at the terminal end of a nerve conduction pathway) are stimulated to treat many different health problems. For example, there are recent studies showing that invasive (e.g., via an implanted electrode) vagus nerve electrical stimulation can treat arthritis, psoriasis, inflammatory bowel disease, colitis, kidney disease, heart disease, diabetes, injury related to cardiopulmonary resuscitation (CPR), ischemic reperfusion injury, sepsis, virus infections, etc. Furthermore, it has been shown that the spleen can be an important component for causing anti-inflammatory effects that are modulated by the vagus nerve, and it is in the spleen that cytokine production and inflammatory cell migration can be modulated.

Nevertheless, while electrically stimulating the vagus nerve has been used to treat many diseases, there may be drawbacks to this approach. The vagus nerve is connected to a multitude of organs or structures in the body (i.e. heart, lung, liver, stomach, kidney, intestines, pancreas, lymph nodes, and spleen) such that electrically stimulating the vagus nerve can result in unintended downstream effects. In one recent clinical study using an implantable vagus nerve stimulator to treat rheumatoid arthritis, the list of side-effects reported by patients included fatigue, dysphonia, hypoesthesia, dizziness, nausea, constipation, dyspnea, and headache.

Some bioelectronics use noninvasive ultrasound with a goal of stimulating one of the end-organs of the vagus-nerve pathway, such as the spleen, to alter or interact with the immune response in the body. There are many advantages in using ultrasound stimulation of the spleen over vagus nerve electrical stimulation. This noninvasive stimulation modality can trigger similar anti-inflammatory effects as those induced using electrical vagus nerve stimulation, without the need for implantation of an electrical stimulation device and without stimulating the rest of the organs in the body. Ultrasound stimulation of the spleen has the potential to provide anti-inflammatory therapy for a wide range of diseases while greatly reducing side-effects. However, to provide the most effective therapeutic outcomes, it may be helpful to focus the ultrasound on the spleen (or other intended organs) or within the projection area of the splenic nerve and not on neighboring organs or interstitium of the abdomen. Nevertheless, focusing the ultrasound can be a challenging task since the spleen is in different anatomical positions and depths from person to person (based on parameters including body type, size, body position, and anatomical variations). Moreover, since one surface of the spleen faces the diaphragm, the spleen is in almost constant motion during typical breathing, which makes continuous targeting of the spleen challenging.

Various embodiments of the present disclosure can be carried out using a wearable device such as that disclosed in pending international application PCT/US21/30464, filed May 3, 2021, and titled "Wearable Focused Ultrasound Phased Array Device for Neuromodulation," which is incorporated by reference in its entirety. Embodiments of the present disclosure may be used in conjunction with one or more embodiments described in pending international application PCT/US21/30464 for the purpose of delivering the desired medical therapies as discussed.

The present disclosure addresses the aforementioned challenges of targeting the spleen and other organs (e.g., the liver, pancreas, or stomach) by providing systems and methods for organ-targeting across different subjects and body positions, as well as during typical spleen motion due to respiration and body movements. In some non-limiting embodiments, disclosed herein are a number of novel biosensor feedback signals and mechanisms that can be used to successfully target the spleen. Embodiments of the present disclosure include a number of methods for incorporating spleen-targeting in a wearable, noninvasive ultrasound therapy device. Embodiments described can be applied to treat a wide range of inflammatory disorders, for example, Crohn's disease, sepsis, acute kidney injury, arthritis, multiple sclerosis, psoriasis, inflammatory bowel disease, colitis, kidney disease, heart disease, injury related to cardiopulmonary resuscitation (CPR), ischemic reperfusion injury, sepsis, virus infections, and other inflammatory conditions, as well as treatment of neurally-regulated systems, for example, diabetes through insulin delivery control, peripheral nerve stimulation/suppression for pain and related indications (e.g., craniofacial pain, migraines, carpal tunnel disorder, sciatica, lower and upper back pain), and pelvic health disorders (e.g., overactive bladder and incontinence).

Although the various disclosed embodiments use the spleen as an example organ, the procedures disclosed herein are generally applicable for use on various organs, including abdominal organs, since the various organs may be located, tracked, and targeted with ultrasound therapy in a similar manner to the spleen. Abdominal organs such as the spleen are attached to the body by fascia which permits a certain amount of movement of the organ within the abdominal cavity; this movement of the abdominal organ can occur as a result of the subject moving (e.g., walking, running, etc.) as well as from movement of the diaphragm (e.g., during breathing). As is shown herein for the spleen, the location and movement of other organs (e.g. abdominal and/or thoracic organs) can be characterized and determined before and during therapy in order to properly direct ultrasound energy at the organ while therapeutic ultrasound is being administered. Other modifications to the disclosed procedures can also be made to account for the other organ's locations within the thorax or abdomen (e.g., the wearable device may be placed in different locations around the torso region) as well as the organ's tendency to shift or move during breathing or other movements of the subject, modifications which are within the level of those skilled in the art.

Biosensor Feedback

1. It has been determined that the spleen moves in a predictable manner during breathing, and spleen motion has been measured during different body positions and breath depths (see example in FIG. 1). This is due to the diaphragm pushing the spleen distally during inspiration (rightwards in the image; head is to the left and feet are to the right). By analyzing ultrasound imaging videos of the spleen, we were able to characterize spleen movement for those situations, as is summarized in Table 1. The spleen may travel a much greater distance during a large breath compared to during a normal breath (e.g., between 63-142% further, depending on body position). For example, in a seated position, the spleen was measured to move 11.1 mm during a normal at-rest breath, but 26.9 mm during a large, deep breath. In addition, the depth of the spleen below the surface of the skin may vary for different body positions, and in some positions the spleen gets deeper during inhalation (see Table 1).

TABLE 1

Measuring Splenic Motion During Breathing using Ultrasound.

| | Cause of motion | Distance spleen moved (mm) | Change in movement of spleen in this position compared to sitting | Change in movement of large breath compared to small | Spleen depth from transducer during exhale (mm) | Spleen depth from transducer during inhale (mm) | Change in spleen depth from transducer during breath |
|---|---|---|---|---|---|---|---|
| Sitting | Heartbeat | 1.7 | — | — | — | — | — |
| Sitting | Normal breath | 11.1 | — | | 8.9 | 8.9 | 0% |
| Sitting | Large breath | 26.9 | — | 142% | 8.9 | 8.9 | 0% |
| Laying right side | Normal breath | 12.1 | 9% | | 15.4 | 16.8 | 9% |
| Laying right side | Large breath | 22.9 | −15% | 89% | 12.4 | 16.3 | 31% |
| Laying on back (supine) | Normal breath | 18.9 | 70% | | 11.6 | 11.6 | 0% |
| Laying on back (supine) | Large breath | 30.8 | 14% | 63% | 13.2 | 13.2 | 0% |

TABLE 1-continued

Measuring Splenic Motion During Breathing using Ultrasound.

| | Cause of motion | Distance spleen moved (mm) | Change in movement of spleen in this position compared to sitting | Change in movement of large breath compared to small | Spleen depth from transducer during exhale (mm) | Spleen depth from transducer during inhale (mm) | Change in spleen depth from transducer during breath |
|---|---|---|---|---|---|---|---|
| Laying on front (prone) | Normal breath | 8.8 | −21% | | 11.4 | 11.4 | 0% |
| Laying on front (prone) | Large breath | 21.1 | −22% | 140% | 10.7 | 11.6 | 8% |

Figure 2:
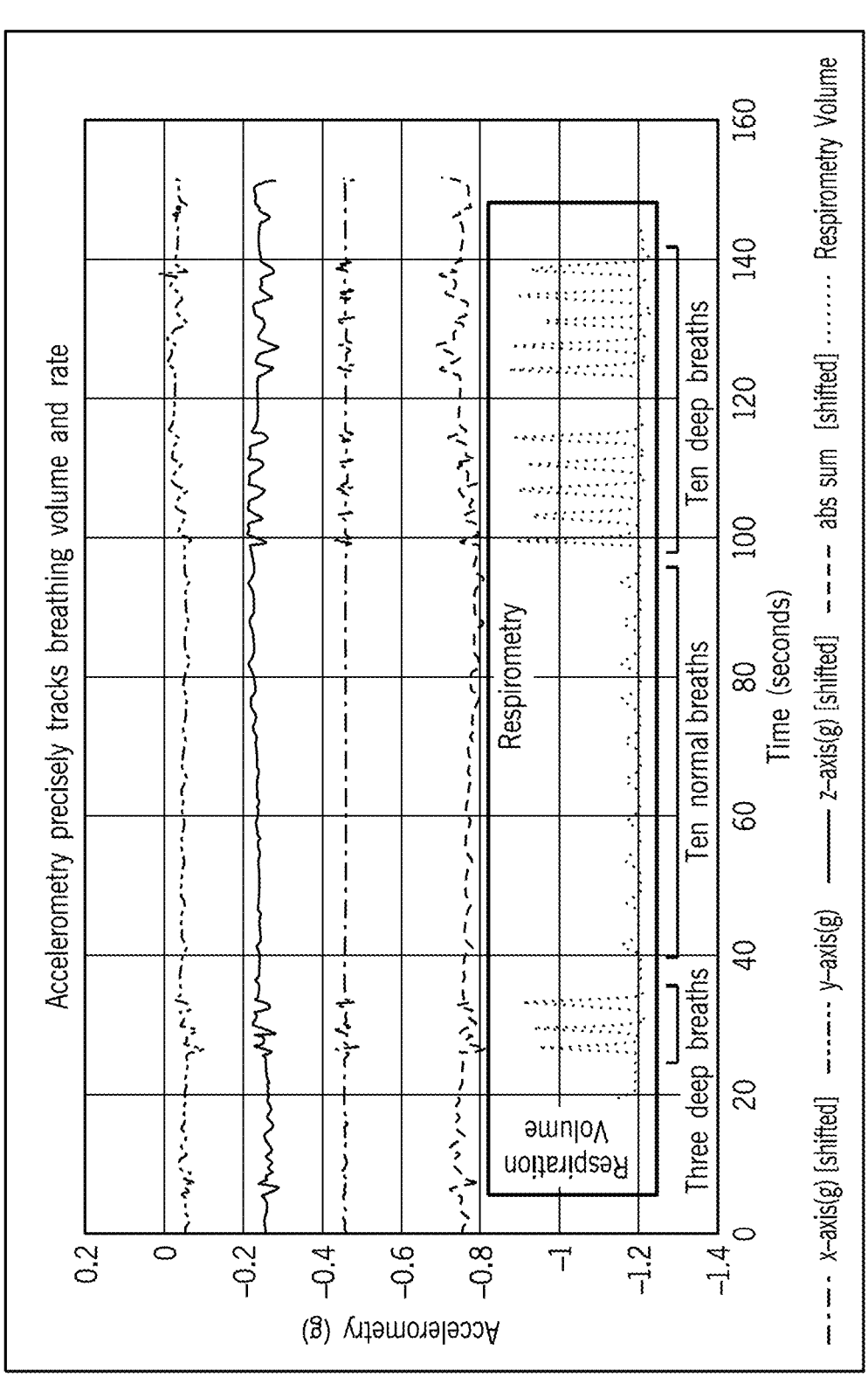
FIG. 2 shows recordings from accelerometers and respirometers which indicate that the accelerometers accurately track breathing volume and rate.
Figure 3:
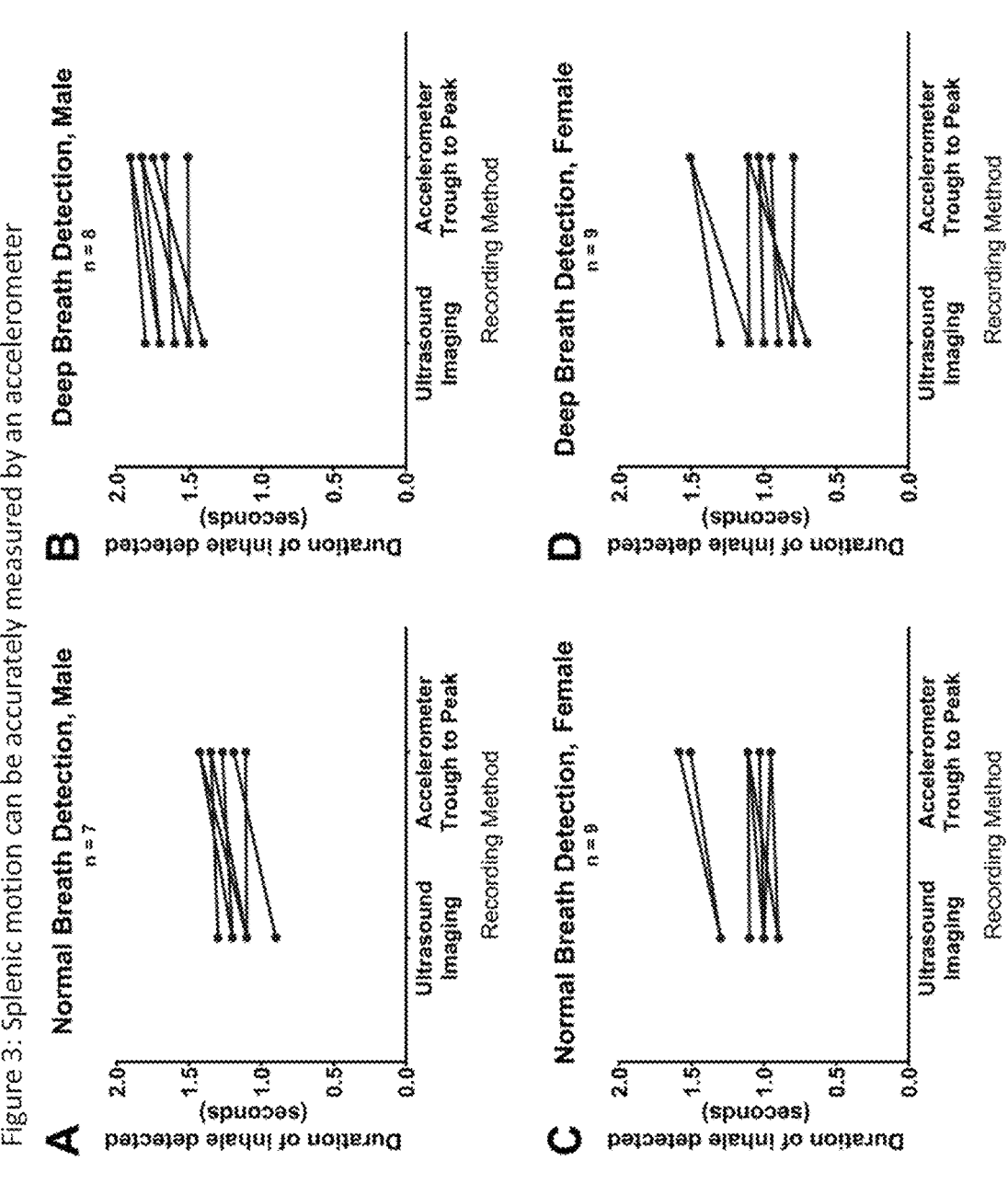
FIG. 3 shows data which indicates that splenic motion can be accurately measured by an accelerometer. Panel A shows normal breath detection for a male, Panel B shows deep breath detection for a male, Panel C shows normal breath detection for a female, and Panel D shows deep breath detection for a female.

2. An accelerometer sensor affixed to the chest can track breathing. Simultaneous recordings from a respirometry sensor belt (used to measure breathing volume) and an accelerometer affixed to the chest (used to measure precise chest motions), demonstrate that breathing volume and breathing rate track very well with the motions recorded by the accelerometer (FIG. 2).

3. An accelerometer sensor affixed to the chest can measure the motion of the spleen due to breathing. Ultrasound imaging of the spleen was performed and recorded simultaneously from an accelerometer affixed to the chest. This showed that accelerometer motion due to breathing directly correlates to splenic motion (FIGS. 3A-3D, Tables 2-5). A total of 33 breaths from male and female subjects were analyzed and the trough-to-peak measurement of the breath as determined by accelerometry closely matched the exhale-to-inhale spleen motion as determined by ultrasound imaging. In fact, the average difference between spleen motion as recorded by ultrasound imaging and spleen motion as determined by accelerometry (e.g., as indicated by inspiration time in each case) could range for example from 0.10-0.18 seconds, with a standard deviation ranging from 0.11-0.17 seconds as shown in Tables 2-5. In addition, the combination of the distance the spleen moved (e.g., as measured using ultrasound imaging, FIG. 1) along with the time of spleen movement (FIGS. 3A-3D, Tables 2-5) was used to determine rate of spleen motion, where this rate can be used to accurately target the spleen during motion. For example, for at-rest breathing with a male subject it was determined that the rate of spleen motion is 9.83 mm/s, information which can be used as part of a procedure to track the spleen during ultrasound stimulation.

TABLE 2

Normal Breath Male Subject.

| Spleen Motion Recordings | Ultrasound Imaging Inspiration Time (s) | Accelerometer Trough to Peak Inspiration Time (s) | Difference between methods (s) |
|---|---|---|---|
| Number of values | 7 | 7 | 7 |
| Minimum | 0.90 | 1.11 | 0.01 |
| 25% Percentile | 1.10 | 1.19 | 0.05 |
| Median | 1.10 | 1.35 | 0.23 |
| 75% Percentile | 1.20 | 1.43 | 0.29 |
| Maximum | 1.30 | 1.43 | 0.33 |
| Mean | 1.13 | 1.30 | 0.18 |
| Std. Deviation | 0.13 | 0.12 | 0.13 |
| Std. Error of Mean | 0.05 | 0.05 | 0.05 |

TABLE 2-continued

Normal Breath Male Subject.

| Spleen Motion Recordings | Ultrasound Imaging Inspiration Time (s) | Accelerometer Trough to Peak Inspiration Time (s) | Difference between methods (s) |
|---|---|---|---|
| Lower 95% CI of mean | 1.01 | 1.19 | 0.06 |
| Upper 95% CI of mean | 1.25 | 1.42 | 0.29 |

TABLE 3

Deep Breath Male Subject.

| Spleen Motion Recordings | Ultrasound Imaging Inspiration Time (s) | Accelerometer Trough to Peak Inspiration Time (s) | Difference between methods (s) |
|---|---|---|---|
| Number of values | 8 | 8 | 8 |
| Minimum | 1.40 | 1.51 | 0.01 |
| 25% Percentile | 1.50 | 1.67 | 0.07 |
| Median | 1.60 | 1.79 | 0.12 |
| 75% Percentile | 1.70 | 1.89 | 0.30 |
| Maximum | 1.80 | 1.91 | 0.35 |
| Mean | 1.60 | 1.76 | 0.16 |
| Std. Deviation | 0.13 | 0.14 | 0.13 |
| Std. Error of Mean | 0.05 | 0.05 | 0.04 |
| Lower 95% CI of mean | 1.49 | 1.64 | 0.05 |
| Upper 95% CI of mean | 1.71 | 1.87 | 0.26 |

TABLE 4

Normal Breath Female Subject.

| Spleen Motion Recordings | Ultrasound Imaging Inspiration Time (s) | Accelerometer Trough to Peak Inspiration Time (s) | Difference between methods (s) |
|---|---|---|---|
| Number of values | 9 | 9 | 9 |
| Minimum | 0.90 | 0.95 | −0.05 |
| 25% Percentile | 0.95 | 0.99 | 0.02 |
| Median | 1.00 | 1.11 | 0.05 |
| 75% Percentile | 1.20 | 1.31 | 0.21 |
| Maximum | 1.30 | 1.59 | 0.29 |
| Mean | 1.06 | 1.16 | 0.10 |
| Std. Deviation | 0.15 | 0.23 | 0.11 |
| Std. Error of Mean | 0.05 | 0.08 | 0.04 |
| Lower 95% CI of mean | 0.94 | 0.98 | 0.01 |
| Upper 95% CI of mean | 1.17 | 1.33 | 0.19 |

US 12,611,555 B2

13

TABLE 5

| Spleen Motion Recordings | Ultrasound Imaging Inspiration Time (s) | Accelerometer Trough to Peak Inspiration Time (s) | Difference between methods (s) |
|---|---|---|---|
| Number of values | 9 | 9 | 9 |
| Minimum | 0.70 | 0.79 | −0.01 |
| 25% Percentile | 0.80 | 0.99 | 0.02 |
| Median | 1.00 | 1.03 | 0.05 |
| 75% Percentile | 1.10 | 1.31 | 0.32 |
| Maximum | 1.30 | 1.51 | 0.41 |
| Mean | 0.97 | 1.12 | 0.15 |
| Std. Deviation | 0.19 | 0.24 | 0.17 |
| Std. Error of Mean | 0.06 | 0.08 | 0.06 |
| Lower 95% CI of mean | 0.82 | 0.94 | 0.02 |
| Upper 95% CI of mean | 1.11 | 1.31 | 0.28 |

Deep Breath Female Subject.

Figure 4:
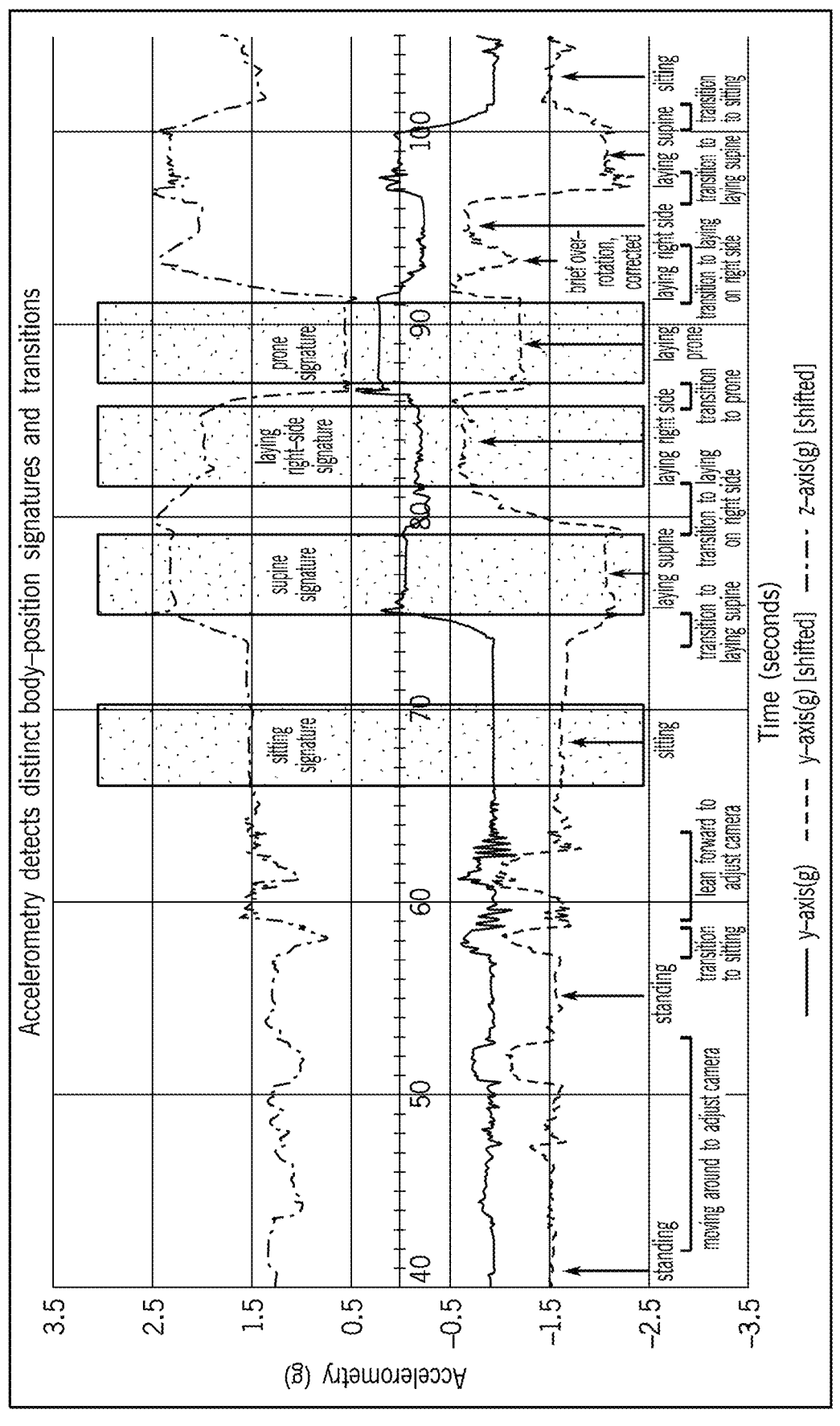
FIG. 4 shows that accelerometry signals produce distinct body position signatures and transitions.

4. An accelerometer sensor affixed to the chest can detect distinct body-positions and transitions between positions. FIG. 4 shows that each body position is associated with a unique accelerometry signature which can be used to identify the body position of the subject who is wearing the accelerometer. When a person with an accelerometer fixed to the chest changes positions, these position signatures can be detected (Standing, Sitting, Lying on back [supine], Lying on right side, Lying on stomach [prone]). When paired with the embodiments from Table 1, which indicate that the spleen motion is unique for each of these positions, the accelerometer may be used to determine position and unique spleen-motion trajectory.

Figure 6:
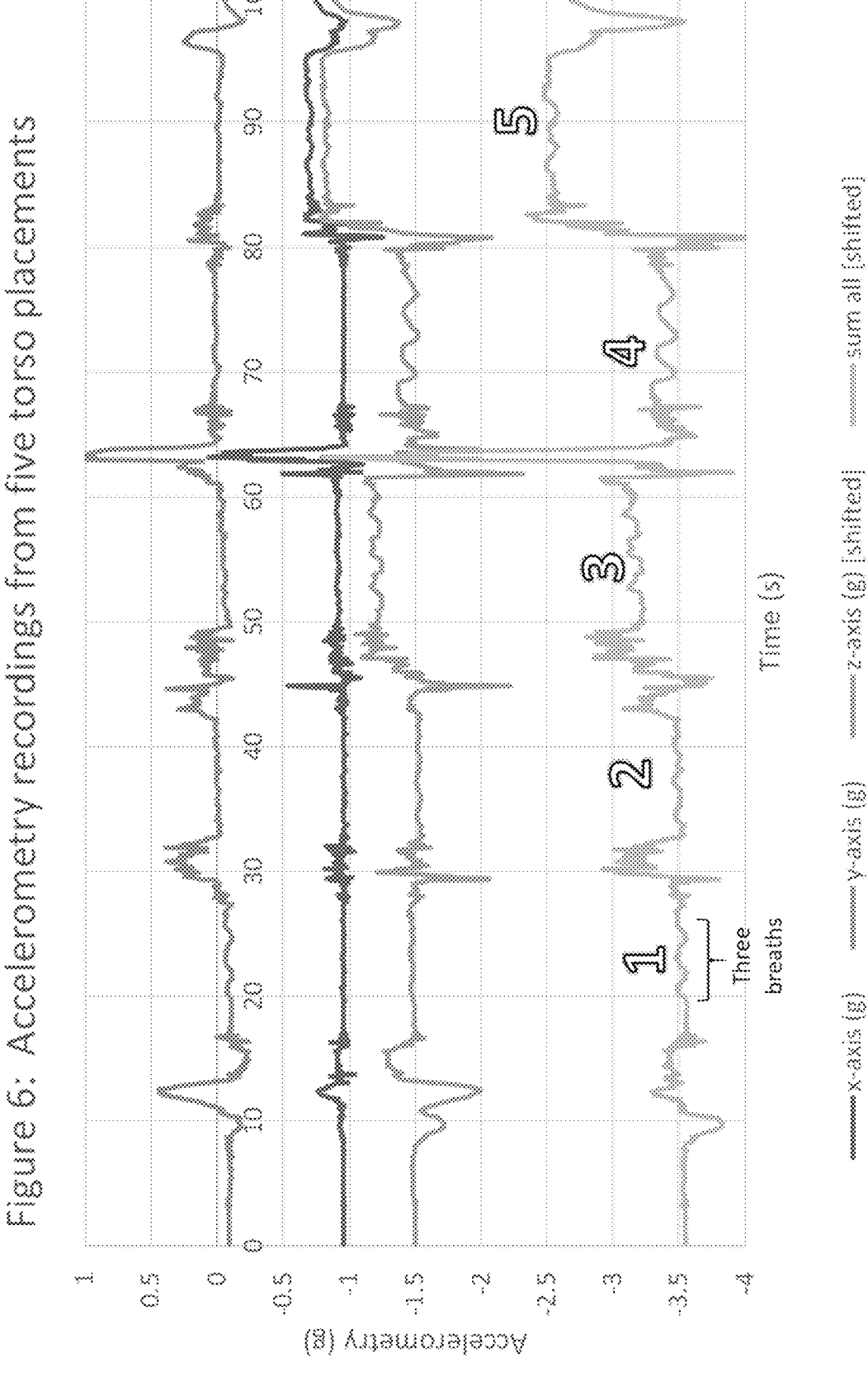
FIG. 6 shows accelerometry recordings associated with each of the five different locations on the torso as shown in FIG. 5 where the subject took three breaths at each accelerometer position.

5. Five placements of the accelerometer on the torso that can be used to record breath and spleen motion are each marked with an "X" in FIG. 5:

1) Placement over costal margin (on edge of rib cage)
2) Side placement (over spleen)
3) Above pectoral muscle
4) On lower abdomen
5) On collar bone area FIG. 6 shows accelerometry recordings associated with the accelerometer when placed in each of the five torso positions, which were recorded during three breaths. Breathing could clearly be detected at each of these locations.

Figure 7:
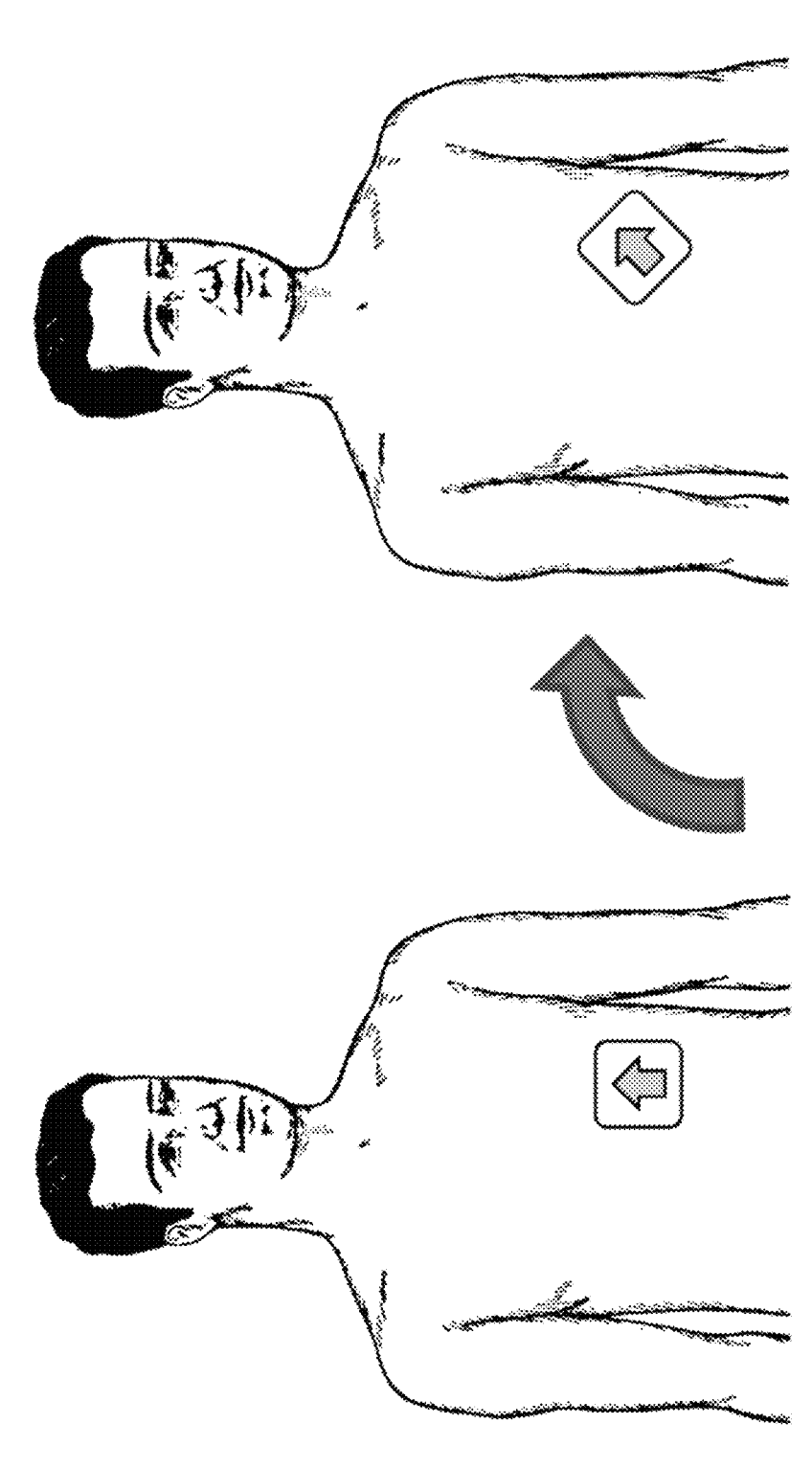
FIG. 7 shows how an accelerometer can be used to track breathing and spleen motion in different orientations.

6. An accelerometer can be used to track breathing and spleen motion in different orientations and as a result the accelerometer does not have to be attached to the subject in a particular orientation. The accelerometer can be affixed to the chest in a vertical position, or may be rotated to a new angle relative to the initial vertical orientation, and the accelerometer may accurately detect breathing and spleen motion. This new angle, for example, could match the angle of the ribs over the spleen (approximately 45° from vertical), or be any angle in between (FIG. 7). In some non-limiting embodiments, as long as the accelerometer remains fixed in the same position on the chest, breathing and spleen motion may be detected from various initial orientation by analyzing the change in motion of the chest wall.

Figure 8:
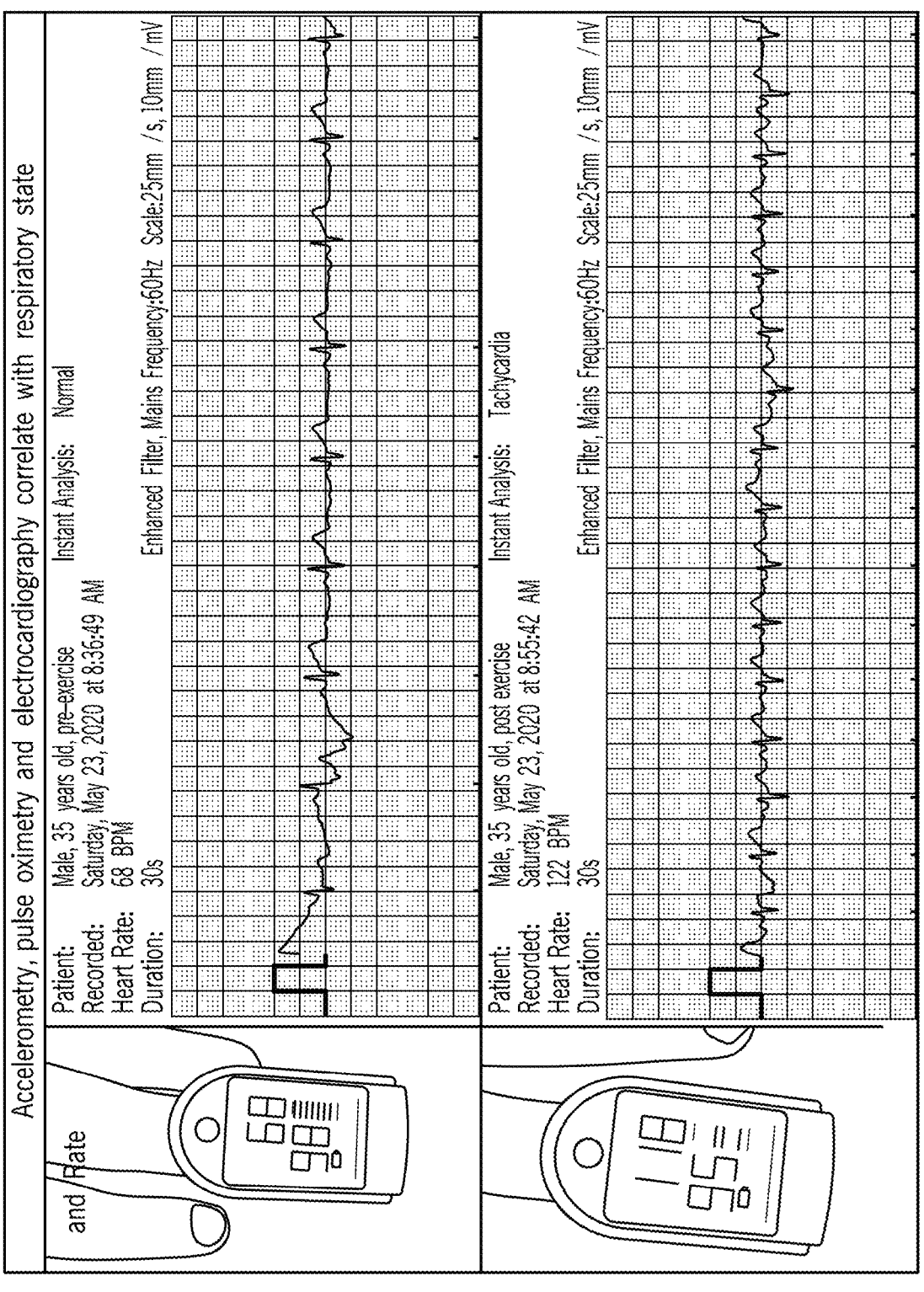
FIG. 8 shows how pulse oximetry and electrocardiography produce data that correlate with respiratory state and which agree with data obtained from accelerometry.

7. One or more of accelerometry, pulse oximetry, and/or electrocardiography (or other ionically- or electrically-evoked signals in the body relating to muscle/tissue movement or alterations such as electromyography (EMG)) may be used alone or together to detect a subject's respiratory state (FIG. 8). FIG. 8 shows 8 s of electrocardiography data in which the square pulse at the beginning of each electrocardiography trace represents 1 mV (height) and 0.2 s (width). The data obtained using pulse oximetry and electrocardiography agree with data obtained from accelerometry, indicating that pulse oximetry and/or electrocardiography can be used along with, or in place of, accelerometry to monitor the subject's breathing, which in turn can be used to determine the organ location. At rest, a subject exhibits a low respiration rate, low heart rate, and high oxygen saturation. In various embodiments, this at-rest state is preferable for spleen stimulation because there is the least number of breaths, and the frequency and distance of spleen motion is minimized; nevertheless, organ stimulation can be carried out in a number of physiological states. At rest, for example, 9.75 breaths per minute were detected using accelerometry, 98% SpO2 using pulse oximetry, and 68 beats per minute heart rate using electrocardiography. In contrast, during an excited respiratory rate (e.g., caused by recent exercise, emotional/psychological state, or acute coughing/illness), a person may exhibit high breathing rate, high heart rate, and reduced oxygen saturation. This excited state can lead to a higher number of breaths, and the frequency and distance of spleen motion may be increased. After exercise, 24.45 breaths per minute were detected using accelerometry, 95% SpO2 using pulse oximetry and 122 beats per minute heart rate using electrocardiography (or other ionically- or electrically-evoked signals in the body relating to muscle/tissue movement or alterations such as electromyography (EMG)). Therefore, the alterations in spleen motion related to exercise or other activity should be tracked when one intends to stimulate the organ with ultrasound energy. In some non-limiting embodiments, these biosensor metrics can be used to correlate average spleen motion. As used herein, the terms "correlate" and "correlation" broadly refer to relationships between parameters that may be identified in various ways and are not limited to a specific mathematical function (i.e., these terms are not limited to, for example, a cross-correlation or other specific function). In some non-limiting embodiments, these measurements can be used to a) support spleen tracking algorithms and/or b) be used as a cutoff for safe or effective spleen stimulation (i.e. report back to the user/administrator/software controller the increased state for adjusting the algorithms and/or temporarily shut down the ultrasound delivery system until a more preferable respiratory state has been achieved).

According to non-limiting embodiments, systems and methods described herein may address the aforementioned challenges of targeting the spleen with ultrasound stimulation therapy during respiratory motion. Some non-limiting embodiments provide a method of splenic targeting across different subjects and body positions as well as during typical spleen motion during respiration. In addition, a number of novel biosensor feedback signals and mechanisms are disclosed which can be used to successfully target the spleen. In some non-limiting embodiments, systems are disclosed to incorporate spleen-targeting in a wearable, noninvasive ultrasound therapy device.

In various embodiments, one or more of the following procedures may be used to determine or estimate a location of an organ such as the spleen of a subject and to facilitate tracking of the organ in order to direct therapeutic ultrasound towards the organ while the subject goes about their normal daily activities: estimating or determining the location based on biophysical and demographic information for the subject; estimating or determining the location based on a baseline recording of the subject's organ during respiratory motion in various body positions and while one or more biosensors is attached to the subject; estimating or determining the location based on ultrasonic reflections at lower energy delivery frequencies or elasticity/elastography measurements to displace the tissue and measure the displacement to identify the tissue type, possibly with use of machine learning; estimating or determining the location based on ultrasound-resolved border-detection of the organ. In various embodiments, the one or more biosensors may include accelerometers, a respiratory belt, electrocardiography leads, a pulse oximeter, and/or an ultrasound transducer.

Biophysical or Demographic Information

According to non-limiting embodiments, described herein is a method for targeting the spleen with ultrasound stimulation therapy formulated on the subject's physical, biophysical and demographic information (age, sex, race, height, weight, rib spacings, circumference of chest, circumference of waist, dimensions of organ, distances of organ to body surface, heart rates, breathing rates, breathing volumes, pre-existing conditions or disease state, etc.). The subject's baseline data may be extrapolated to fit population data that has been collected to determine expected spleen motion during respiration for a particular population set, body position, and respiration state. The subject may undergo a preliminary fitting session in which a baseline physical assessment is performed to collect physical, biophysical and demographic information, and/or a baseline abdominal ultrasound imaging and ultrasound video recording session (e.g., using a commercial ultrasound imaging device) may be conducted to determine spleen location, depth, and respiratory motion of the spleen in various body positions (e.g., standing, sitting, lying prone, moving (e.g., shifting orientation), etc.) and various breathing volumes. The skin may be marked (e.g., using henna, permanent ink markers, or other durable marking materials or procedures) over the spleen for future placement of a wearable ultrasound-therapy device which can provide focused steering of ultrasound energy to different locations in the body. Based on the imaging of the spleen, the device can be programmed to target the spleen in a still position. Based on the subject's unique physical and biophysical characteristics, the therapy may be tailored in a way which is unique to the subject and may include administering ultrasound stimulation that targets and tracks with the spleen during motion. The real-time feedback system including various sensors can also temporarily switch the device off and alert the user/administrator/ software controller if the subject's respiratory state and/or body position is not preferable for stimulation, or an abnormal physiological condition is detected.

Baseline Recordings of Organ Location

According to non-limiting embodiments, described herein is a method for targeting the spleen with ultrasound stimulation therapy formulated on a baseline recording of the subject's spleen during respiratory motion in various body positions. The subject may undergo a preliminary fitting session in which a baseline physical assessment is performed to collect physical, biophysical and demographic information (age, sex, race, height, weight, rib spacings, circumference of chest, circumference of waist, dimensions of organ, distances of organ to body surface, heart rates, breathing rates, breathing volumes, pre-existing conditions or disease state, etc.) and/or baseline abdominal ultrasound imaging and ultrasound video recording session (e.g., using a commercial ultrasound imaging device) to determine spleen location, depth and respiratory motion of the spleen in various body positions (e.g., standing, sitting, lying prone, moving (e.g., shifting orientation), etc.) and various breathing volumes. The skin may be marked (e.g., using henna, permanent ink markers, or other durable marking materials or procedures) for future placement of a wearable ultrasound-therapy device, which can provide focused steering of ultrasound energy to different locations in the body. From baseline imaging of the spleen using a commercial ultrasound device, the device can be programmed to target the spleen in a still position. The ultrasound-therapy device may further be programmed to incorporate real-time data from accelerometry, pulse oximetry, and electrocardiography (or other ionically or electrically-evoked signals in the body relating to muscle/tissue movement or alterations such as electromyography (EMG)) in combination with the subject's baseline ultrasonography datasets, leveraging the correlations, relationships, and parameters demonstrated in the data presented herein. Based on the subject's unique physical and biophysical characteristics and the baseline dataset measuring how the spleen moves during respiration, the therapy may be tailored so that it is unique to the subject and may include administering ultrasound stimulation that targets and tracks with the spleen during motion. For example, the time of accelerometer motion from peak to trough can be used to steer the ultrasound beam from max distance of spleen locations between inhale and exhale breathing cycles. The slope or derivative of the accelerometer motion can also be used to adjust the rate of steering of the ultrasound beam. The real-time feedback system can also temporarily switch the device off and alert the user/administrator/software controller if the subject's respiratory state and/or body is not preferable for stimulation, or an abnormal physiological condition is detected. For example, if the subject has their device fitted in a sitting position for treatment and the subject starts to lie down or stand up during treatment, the accelerometer is able to detect that motion and change in body position, as shown above, and thus turn the device off if the ultrasound stimulation conditions are not acceptable. If the respiration rate, pulse oximetry and/or electrocardiography (or other ionically or electrically-evoked signals in the body relating to muscle/tissue movement or alterations such as electromyography (EMG)) signals shows fluctuations that have become too rapid, the device can also turn off stimulation until physiology returns to a reasonable or defined range for each subject.

Ultrasonic Reflections to Measure Tissue Displacement

According to non-limiting embodiments, described herein is a method for targeting the spleen with ultrasound stimulation therapy formulated on ultrasonic reflections at lower energy delivery frequencies (less than 3 MHz) or elasticity/elastography measurements, which utilize energy delivery to displace tissue and diagnostic pulse-echo measurements at higher frequency (1-10 MHz) to measure tissue displacement, correlating displacement with delivered energy to determine elasticity for the purpose of determining the tissue type (e.g., specific organs have a known elastic modulus as compared to surrounding bone, fat or muscle tissue). The subject may undergo a preliminary fitting session in which a baseline physical assessment is performed to collect physical, biophysical, and demographic information (age, sex, race, height, weight, rib spacings, circumference of chest, circumference of waist, dimensions of organ, distances of organ to body surface, heart rates, breathing rates, breathing volumes, pre-existing conditions or disease state, etc.) and/ or baseline ultrasound recordings detected by a wearable device, and standard ultrasonography images/videos (e.g., using a commercial ultrasound imaging device) in various body positions (e.g., sitting, lying prone, moving (e.g., shifting orientation), etc.) and various breathing volumes. The ultrasound stimulation device may be capable of both transmission and reception of ultrasound signals. Signals may be received using bulk-piezoelectric materials (such as PZT in 3-3 mode), piezoelectric micromachined ultrasonic transducers (PMUTs), generally used in 3-1 mode, capacitive micromachined ultrasonic transducers (CMUTs), also generally used in 3-1 mode, or Polyvinylidene fluoride or polyvinylidene difluoride (PVDF) used as a passive receiver. The ultrasound transducer used for reception, or transmission and reception (pulse-echo or pitch-catch), may be single element or multi-channel count phased array transducers, capable of higher or very high resolution. Ultrasound frequencies may vary between 200 kHz to 10 MHz. During baseline recordings the device may be trained to recognize the reflection signal of the spleen during various body positions and various breathing volumes. The ultrasound signals may be reflected from a variety of tissues, including bone, muscle, fibrous tissue, organs (e.g. spleen), and more. In some embodiments, the ultrasound signals may be used to detect blood vessels or nerves/bundles of nerves with or without blood vessels within or near an organ; this information, in conjunction with information about the anatomy of the organ, can be used to target and steer ultrasound energy to the organ or specific regions of an organ. In addition, detection of tissue regions devoid of blood vessels can be used to confirm the identification of a border of an organ or of a location just outside of the organ's border within the abdominal cavity space. In certain embodiments, contrast agents and/or microbubbles can be introduced into the subject's bloodstream to facilitate ultrasonic or other imaging of blood vessels.

Although received ultrasound signals may not necessarily be capable of resolving detailed images in some conditions or for specific anatomical targets, through machine learning techniques and by gathering significant information, correlation of spleen position using the received signals may be achieved. In addition to the reflection signals from the spleen, unique signaling profiles can be additionally generated to sufficiently determine the location of the spleen and motion when combined with the sensor feedback signals as described above. Ultrasonic reflection signals may be used during real-time therapy to target the spleen during respiratory motion. During preliminary ultrasound imaging of the spleen, the skin may be marked as noted above for future placement of a wearable ultrasound-therapy device. The ultrasound-therapy device may be programmed to incorporate real-time data from ultrasonic reflections, accelerometry, pulse oximetry, and electrocardiography (or other ionically or electrically-evoked signals in the body relating to muscle/tissue movement or alterations such as electromyography (EMG)) in combination with the subjects' baseline ultrasonography datasets. Based on the subject's unique physical and biophysical characteristics and the baseline dataset measuring how the spleen moves during respiration, the therapy may be tailored in a way that is unique to the subject and may include administering ultrasound stimulation that targets and tracks with the spleen during motion. The real-time feedback system can also temporarily switch the device off and alert the user/administrator/software controller if the subject's respiratory state and/or body position is not preferable for stimulation, or if an abnormal physiological condition is detected. In addition, if the subject replaces the device on the skin/rib area and does not exactly align the device to the marked area, then the device can use reflections across several cycles of spleen motion to recalibrate itself to account for the placement discrepancies. This is possible because it can match reflection signals with the other sensor data from the initial device placement to the new misaligned placement to shift the range of distances for beam steering the ultrasound energy to the spleen.

Ultrasound-Resolved Border-Detection

According to non-limiting embodiments, described herein is a method for targeting the spleen with ultrasound stimulation therapy formulated on ultrasound-resolved border-detection of the spleen. The subject may undergo a preliminary fitting session in which a baseline physical assessment is performed to collect physical, biophysical and demographic information (age, sex, race, height, weight, rib spacings, circumference of chest, circumference of waist, dimensions of organ, distances of organ to body surface, heart rates, breathing rates, breathing volumes, pre-existing conditions or disease state, etc.) as well as baseline ultrasound-resolved border-detection of the spleen using a wearable device, and/or standard ultrasonography images/videos (e.g., using a commercial ultrasound imaging device) in various body positions and various breathing volumes. Reflections within the frequency of approximately 1-10 MHz in pulse-echo or pitch-catch mode from the spleen can be used to accurately locate the position of the spleen. This method may be employed using single-element or multi-channel phased array ultrasonic transducers such as those disclosed in international application PCT/US21/30464. In some non-limiting embodiments, a two-dimensional phased array ultrasound transducer may employ synthetic aperture imaging techniques whereby individual channels are activated separately to construct an image of the desired object (e.g., spleen) to improve accuracy and simplify signal processing. Additionally, elasticity may be employed by utilizing the combination of energy delivery capability using a lower frequency (<3 MHz) transducer with a higher frequency (1-10 MHz) receiving transducer. Elasticity uses a mechanical force, which may be provided by the energy delivery transducer to cause deformation in the target tissue (e.g. spleen) while subsequently measuring the displacement of the target tissue and surrounding area to determine strain. With knowledge of the approximate elastic modulus of the target organ, the provided stress divided by the measured displacement can be used to delineate between the target organ and its surrounding tissue and hence to accurately locate the target organ. The ultrasound stimulation device may be capable of resolving spleen location by detecting the edges of the spleen from ultrasound-resolved border detection in different body states. These border-detection signals may then be used during real-time therapy to target the spleen during respiratory motion. These or other methods can also be used to detect blood vessels or bundles of nerves with or without blood vessels within or near an organ, which can be used to target and steer ultrasound energy to the organ or specific regions of an organ. Additionally, tissue regions void of blood vessels can be used to determine when a border of an organ is identified or a location just outside of its border within the abdominal cavity space. In addition, contrast agents and/or microbubbles can be introduced into the subject's bloodstream to facilitate ultrasound or other imaging of blood vessels.

During preliminary ultrasound imaging of the spleen, the skin may be marked (e.g., using henna, permanent ink markers, or other durable marking materials or procedures) for future placement of a wearable ultrasound-therapy device. The ultrasound-therapy device may be programmed to incorporate real-time signals from spleen border-detection, accelerometry, pulse oximetry, and electrocardiography (or other ionically or electrically-evoked signals in the body relating to muscle/tissue movement or alterations such as electromyography (EMG)) in combination with the subject's baseline ultrasonography datasets. Based on the subject's unique physical and biophysical characteristics and the baseline dataset measuring how the spleen moves during respiration, the therapy may be tailored uniquely to the subject and may include administering ultrasound stimulation that targets and tracks with the spleen during motion. The real-time feedback system can also temporarily switch the device off and alert the user/administrator/software controller if the subject's respiratory state and/or body position is not preferable for stimulation, or an abnormal physiological condition is detected. This imaging method can be used to recalibrate the beam steering of ultrasound to the spleen by the device, in which using the imaging methods described above can further enhance this calibration process.

Database

In various embodiments, data from each fitting of a subject as disclosed above may be entered into a database. The data may include physical, biophysical and demographic information about the subject as well as any information regarding the location of the organ (e.g., spleen) within the subject during the fitting, including if available information regarding direct imaging of the organ location as well as biosensor data obtained from one or more of: a wearable ultrasound device, an accelerometer, a pulse oximeter, a respirometer, an electrocardiography (EKG) electrode, an EMG electrode, a wearable fitness device, or other biosensor or motion sensor associated with the subject's body or its physiological responses. In various embodiments, the respirometer or other sensors for measuring the expansion/contraction of the chest, stomach, waist or other torso region can include flexible electronic materials (e.g., piezoresistive materials) and/or textile electrodes for monitoring respiratory activity or other changes in shape or movements of the body.

The database may be developed each time additional information from a subject is added such that the database can be used to speed up the fitting process for subjects in the future. For example, the location of the organ may be determined based on the subject matching some or all of certain physical, biophysical and/or demographic information in the database. This information may be supplemented with data obtained directly from the subject being fitted such as direct imaging of the at-rest location of the organ in the subject. This initial organ location information based on information from the database, along with basic information from the subject such as height, weight and circumference of waist/chest, may be sufficient to program a wearable ultrasound device so that it could track the location of the organ and deliver ultrasound energy to the subject's organ over an extended period of time (e.g., over hours to days to weeks to months) and under a variety of conditions and body positions.

In particular embodiments, a subject may conduct an initial abbreviated fitting based only on demographic information (e.g., height, weight, etc.) and basic biophysical information obtained from one or more accelerometers attached to the subject (e.g., in the torso region). In various embodiments this information may optionally be supplemented with other data such as biosensor data from a wearable ultrasound device, a pulse oximeter, a respirometer, or an EKG electrode, an EMG electrode, a wearable fitness device, or other biosensor or motion sensor associated with the subject's body or its physiological responses.

In some embodiments, additional software may be used to match information from the database with that of a new subject who is being fitted for a wearable ultrasound delivery device. Various techniques including artificial intelligence analysis of the database may be used to develop a system which can accurately predict the location of the subject's organ based on a minimal set of information from the subject so that the time needed for the fitting process can be substantially reduced. In certain embodiments, the time of the fitting process may be reduced from about 1-3 hours to about 10-20 minutes using a predictive system that is based on the database of information from fittings of prior subjects.

As noted above, a complete fitting procedure may require several hours of time in order to collect a complete set of information from the subject under a variety of conditions such as different body positions (e.g., sitting, standing, lying, prone, supine, moving (e.g., shifting orientation), etc.) as well as physiological conditions (e.g., at rest or during movement such as walking or other exercise). In some embodiments, the information collected during a complete fitting procedure may include direct imaging of the organ in each of the positions and/or physiological conditions along with biosensor data from one or more of: a wearable ultrasound device, an accelerometer, a pulse oximeter, a respirometer, an EKG electrode, an EMG electrode, a wearable fitness device, or other biosensor or motion sensor associated with the subject's body or its physiological responses. The imaging of the organ may be performed by the wearable ultrasound device (if suitably equipped) and/or by an external imaging device (e.g., ultrasound, CT, MRI, etc.).

Wearable Ultrasound Device

As noted above, in certain embodiments a wearable ultrasound device which may be used to carry out certain disclosed embodiments may include the device disclosed in pending international application PCT/US21/30464, filed May 3, 2021, and titled "Wearable Focused Ultrasound Phased Array Device for Neuromodulation," which is incorporated by reference in its entirety. In other embodiments, other wearable devices may be used provided the device can direct and steer the ultrasound energy in a variety of different patterns and/or directions (e.g., to account for the location of the ribs and/or movement of the organ during breathing and other movement of the subject). The wearable device may include single-element or multi-channel phased array ultrasonic transducers. In some embodiments, the wearable device may include a two-dimensional phased array ultrasound transducer that may employ synthetic aperture imaging techniques whereby individual channels are activated separately to construct an image of the organ (e.g., the spleen) to improve accuracy and simplify signal processing. In certain embodiments, the wearable device may be configured to perform elasticity/elastography measurements as described above.

In some embodiments, the wearable device may also include a processor, communications, data storage, and/or data processing capabilities so that the device can receive data from various sensors and process the data to determine the organ location at a particular point in time and then determine where to steer the ultrasound energy. The wearable device may be battery-powered and may be in wired or wireless communication with various components including various biosensors. In other embodiments, the sensor and other data may be directed to a separate device (e.g., standalone controller or smartphone) which processes the data and then provides ongoing instructions to the wearable device regarding how to steer the ultrasound energy. Thus, the term wearable ultrasound device may encompass a device in which various components and functions may be contained within a single component or distributed among several elements, some of which may be attached to or associated with the subject's body and some of which (e.g., data collection, storage, and processing elements) may be separate from the subject's body. In various embodiments, the wearable device may include one or more components attached to or hung on the subject's body in the form of a cross sling, a shoulder bag, a chest strap, or an abdomen belt.

Figure 5:
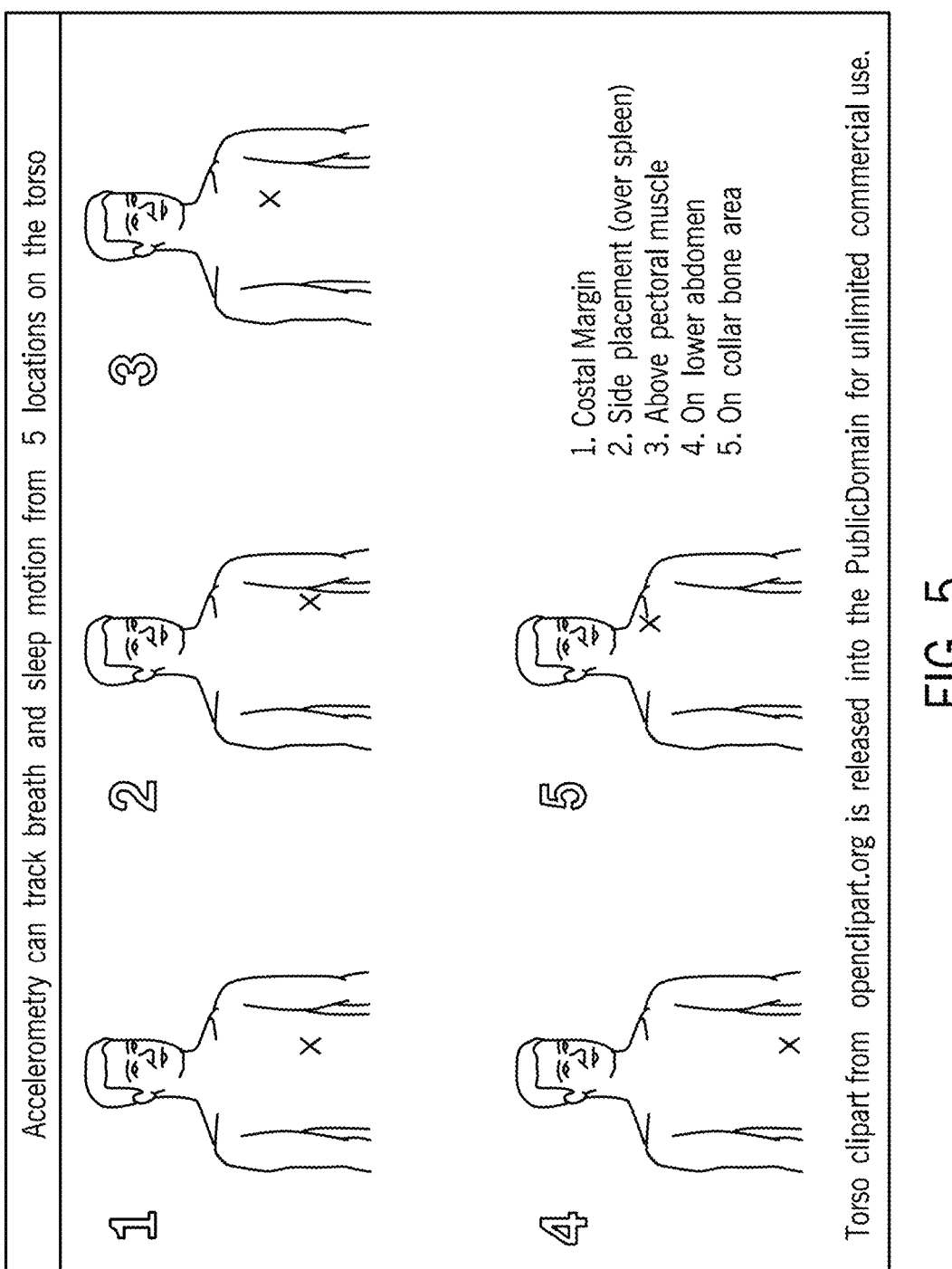
FIG. 5 shows that accelerometry can track breath and spleen motion from five different locations on the torso.
Figure 9A:
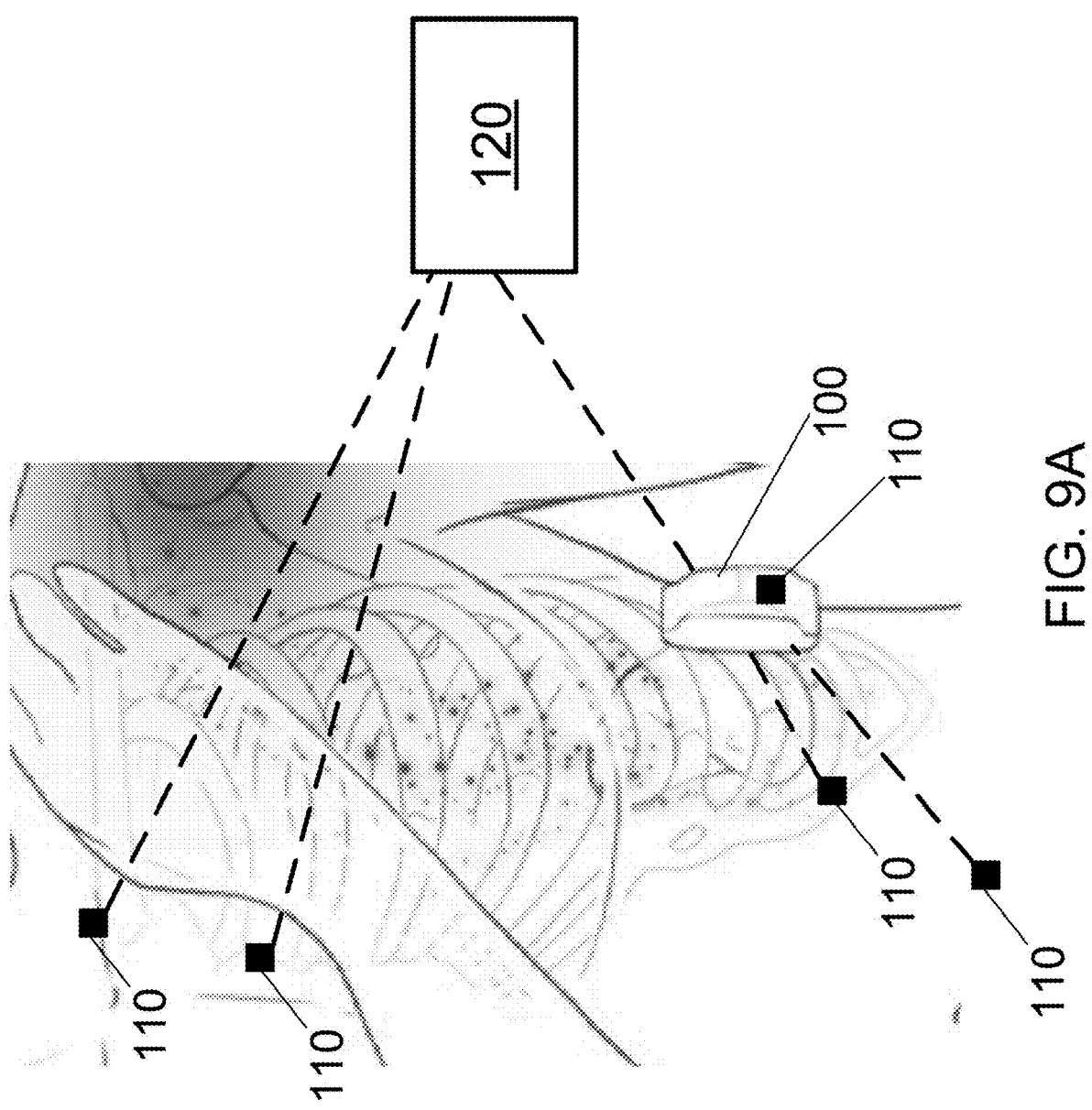
FIGS. 9A-9E show the placement of a wearable ultrasound device and a rib detection procedure.
Figure 9B:
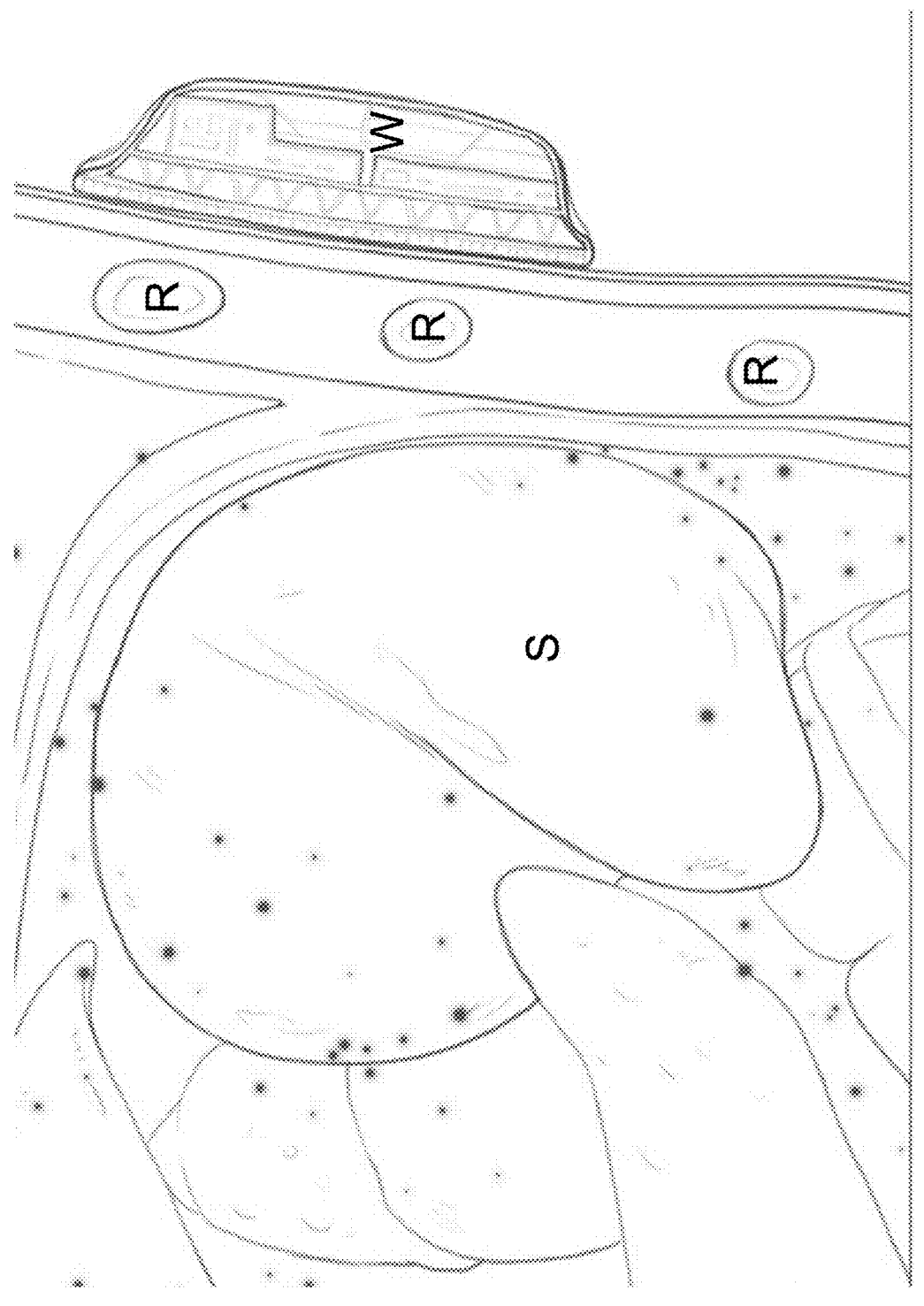

In various embodiments, the wearable device may be associated with one or more accelerometers that are associated with the torso of the subject (e.g., as shown in FIGS. 5 and 9A) and which in some embodiments may be integrated into the wearable device itself. The accelerometers that are not integrated into the wearable device may communicate with the wearable device and/or with a separate base unit in a wired or wireless manner. In certain embodiments, the one or more accelerometers may be arranged on the body of the subject in a manner that permits the system to track movements of the subject's torso (e.g., rib cage expansion and contraction) during breathing and other motions as well as the overall position of the subject's body (e.g., to determine whether the subject is sitting, standing, lying, moving (e.g., shifting orientation), etc.).

As disclosed herein, the accelerometer data may contain patterns including distinct signatures that may be used to determine information such as the subject's body position which in turn can be used to estimate the location of the particular organ (e.g., the spleen). The estimated organ location information can then be used to instruct the wearable device to direct ultrasound energy at the organ. The estimate of the organ location can be updated on a regular basis—(e.g., as often as every second or fraction of a second), approaching a real-time updating of the estimate and subsequent adjustment of the ultrasound energy direction.

In some embodiments the accelerometer data can be supplemented with biosensor data from one or more of: the wearable ultrasound device itself as well as from a pulse oximeter, a respirometer, an EKG electrode, an EMG electrode, a wearable fitness device, or other biosensor or motion sensor associated with the subject's body or its physiological responses. The wearable fitness device may include devices such as a fitness wristband/watch or a heart rate monitor associated with the subject's body. These sensors or additional measurement devices may be part of the ultrasound device or in different locations across the body in wired or wireless communication with the wearable ultrasound device. The additional data from these sensors can be used to determine and/or confirm the subject's physiological state, for example whether the subject is at rest or active and/or breathing quickly or slowly. In certain embodiments, it may be preferable to provide ultrasound stimulation to the subject while they are at rest and breathing slowly, such as 8-20 breaths per minute, with 60-80 heart beats per minute when tracking the location or movement of the organ is more readily possible. In certain embodiments, ultrasound stimulation may be provided when it is determined that the subject is at rest and ultrasound stimulation may be stopped (or not started) when it is determined that the subject is actively moving (e.g., walking, running, or engaging in other ongoing movement).

Based on the initial fitting procedure, the wearable device may be programmed for the particular subject. The programming information may be stored on the wearable device itself and/or on an external device (e.g., a controller, smartphone, or computer system) that is in wired or wireless communication with the wearable device. The programming may provide correlations between biosensor readings and organ locations as determined by direct imaging of the organ and/or based on information in a database of information from previously-fitted subjects. During use the pre-programmed organ prediction correlations may be supplemented with direct measurements of the location of the organ based on other procedures disclosed herein including ultrasound-resolved border detection and ultrasound-based elasticity/elastography measurements of the organ. The direct measurements of organ location, if used, may be performed at irregular or regular intervals (e.g., every 5 seconds, every 10 seconds, every 15 seconds, every 30 seconds, every 60 seconds, or other intervals) to confirm the location of the organ; the frequency with which direct measurements are made may be increased if the subject is breathing heavily or moving about to ensure proper tracking of the organ's location.

Rib Detection

In various embodiments, the wearable device may undergo a procedure for detection of the subject's rib(s) near the ultrasound transducer. FIGS. 9A-9E show placement of a wearable ultrasonic device 100 on the left side of a subject's chest in the vicinity of the spleen. FIG. 9A is a perspective view showing the location of the wearable device 100 and FIGS. 9B-9E are cross-sectional views showing the relative locations of the spleen S (FIG. 9B) and nearby organs, the 9th-11th ribs R, and the wearable device W 100, among other structures. FIG. 9A shows possible locations of biosensors 110 associated with the subject's body such as an accelerometer, a pulse oximeter, a respirometer, an EKG electrode, an EMG electrode, a wearable fitness device, or other biosensor, as well as an external device 120; the external device 120 may be a standalone device such as a controller, smartphone, or computer system. The dashed lines indicate that the biosensors 110 may communicate in a wired or wireless manner with one or both of the wearable device 100 and/or the external device 120. The rib bone R (indicated in FIG. 9B) blocks at least a portion of the ultrasound energy and therefore it is preferable to direct the ultrasound energy through the intercostal space between the ribs. To do this the wearable device may conduct a rib detection procedure as disclosed in pending international application PCT/US21/30464, which is incorporated herein by reference in its entirety.

Figures 9C, 9D, 9E:
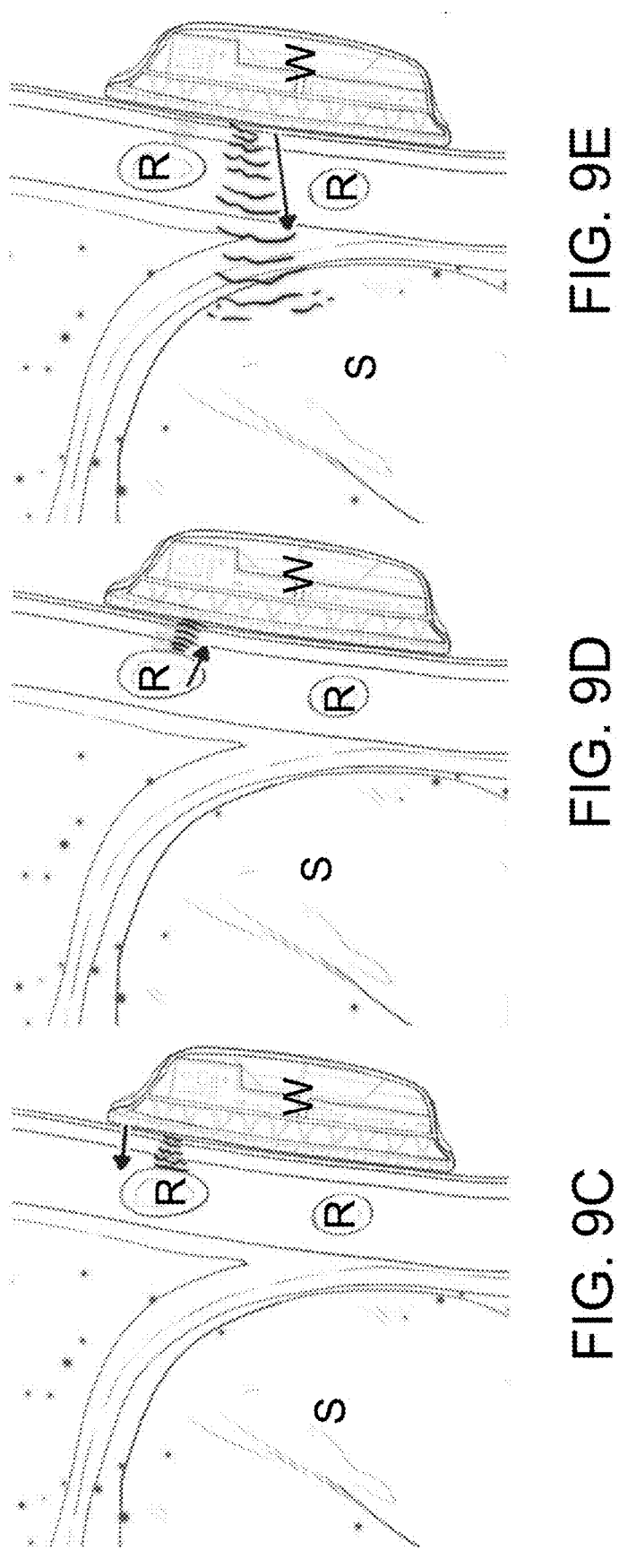

To conduct rib detection, the wearable device emits ultrasonic energy toward the tissue (FIG. 9C) and detects whether ultrasonic energy is reflected back from the tissue (FIG. 9D). Based on the detected reflections (if any) that are received, the wearable device can identify the presence and location of any rib(s) and adjust the ultrasound beam if necessary so that it is directed into the intercostal space between a pair of adjacent ribs (FIG. 9E). In the case where the organ of interest is the spleen (as shown in FIGS. 9A-9E), the wearable device may be placed near the 9th through the 11th ribs on the subject's left side and thus the wearable device may undergo rib detection and perform adjustments to transmit the ultrasound beam between the 9th and 10th ribs or between the 10th and 11th ribs in order to provide ultrasound energy to the spleen. In various embodiments, depending on the subject's particular anatomy, the wearable device may be placed in other locations on the subject's body in order to be able to provide ultrasound stimulation to the spleen or other organ(s).

In certain embodiments, the ultrasonic transducers of the wearable device may extend across a sufficiently large area to span a region covering several ribs along with the intercostal spaces between the ribs (FIGS. 9A-9E). Spanning this amount of space provides added flexibility regarding where the beam can be emitted to allow the ultrasonic device to make adjustments to the location and/or direction of the ultrasonic beam prior to or during treatment; such adjustments may be required if the wearable device changes position relative to the ribs, for example due to the subject changing body position or due to the wearable device being reattached in a slightly different position between therapy sessions. In some embodiments, the wearable device may be placed on the subject's rib cage so that the ultrasonic transducer array (in the case of a linear or rectangular array) is perpendicular to the long axis of the ribs, which allows different elements of the transducer array to be used to stimulate the organ (e.g., the spleen) depending on which elements are aligned with the intercostal spaces between ribs and which elements are aligned directly with the rib bones themselves. In various embodiments, each element in a multi-element ultrasonic transducer array may be used as a transmitter, a detector, or both in the rib detection procedure as well as during other functions performed by the wearable device.

Delivery of Therapeutic Ultrasound

In use, the wearable device along with any additional sensors associated with the subject's body allow the subject to receive ultrasound therapy in a non-invasive and minimally-intrusive manner. To begin therapy, the subject may attach the wearable device to their chest or abdominal region at a location determined during an initial fitting procedure which may be designated using skin markings. The wearable device may be attached using tape (e.g., medical tape) or adhesives or may be held in place using elastic bands or bandages. Other biosensors may be integrated into the wearable device and/or may be separately attached to the subject's skin also using tape, adhesives, bands, and/or bandages as needed. These different sensors could also be implanted into different body regions or could be positioned in a minimally invasive manner underneath or through the skin surface. The wearable device may be a standalone system which collects and processes data from the biosensors and from the ultrasound transducer/detector array or the wearable device may be in communication with an external device which performs some or all of the data collection and processing functions.

Figures 10A, 10B, 10C:
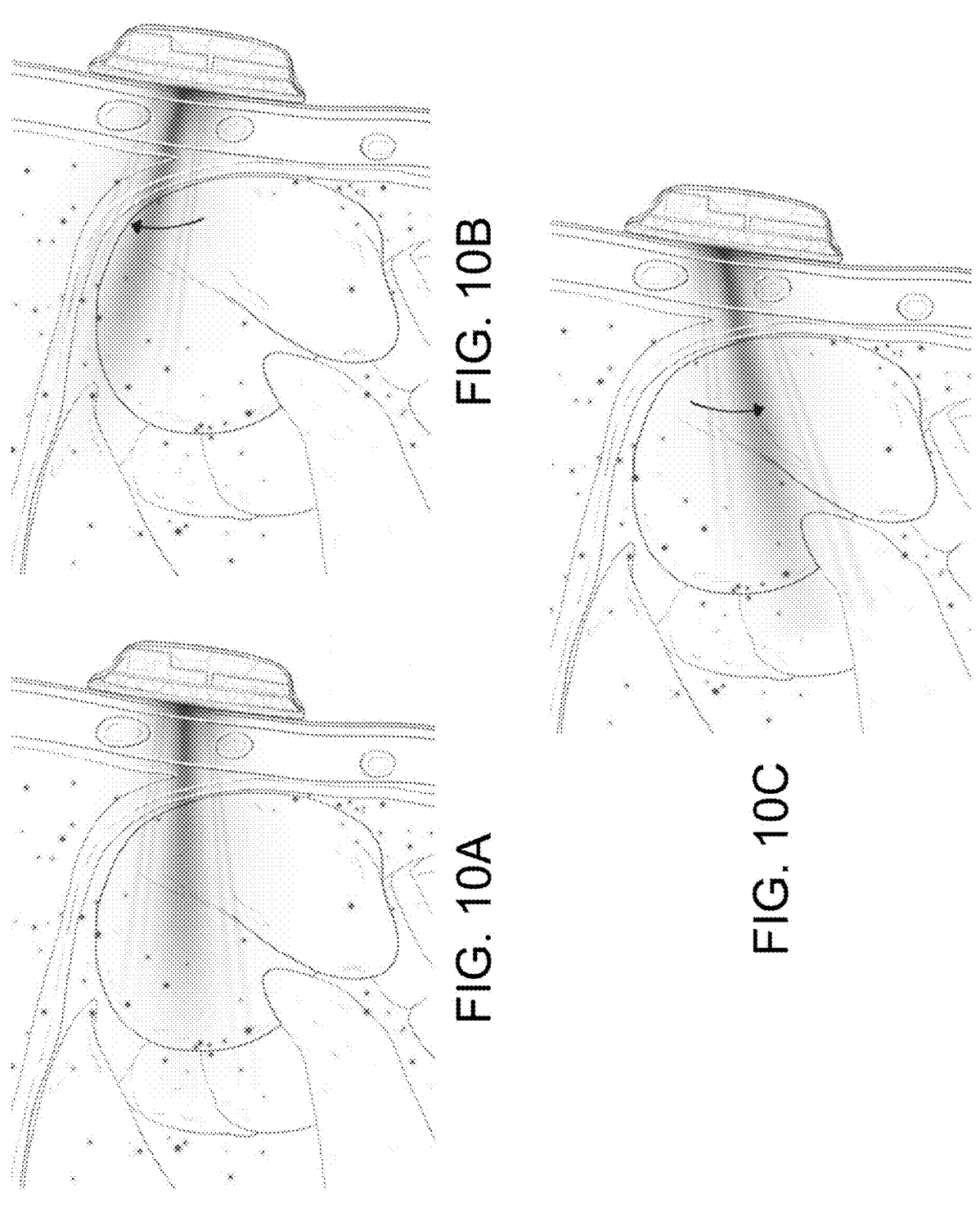
FIG. 10A shows a wearable ultrasonic device directing a beam of ultrasonic energy towards the spleen in a subject's chest.
FIG. 10B shows the wearable ultrasonic device steering the beam of ultrasonic energy upwards (arrow)
FIG. 10C shows the wearable ultrasonic device steering the beam of ultrasonic energy downwards (arrow).

The device and associated sensors are able to collect data from the subject while the subject goes about their normal activities and are thereby able to integrate ultrasound therapy into the subject's normal daily schedule with minimal inconvenience. In various embodiments, the therapeutic ultrasound may be applied at least once per day for at least 9 minutes; in some embodiments, the therapy may be delivered for at least 15 minutes, at least 20 minutes, at least 30 minutes, at least 60 minutes, or other amounts of time as needed. Therapy may be applied on a daily basis, every other day, every week, or other time periods as needed. The therapy session can be performed in shorter periods, such as 3-minute sessions or 5-minute sessions that are repeated multiple times consecutively or with a break between sessions depending on the needs of treatment or application. A range of ultrasound stimulation parameters may be used, for example as disclosed in international application PCT/US2021/014583, filed Jan. 22, 2021, and titled "Systems and Methods for Responsive Ultrasound Stimulation for Immuno-Modulation Treatment," which is incorporated herein by reference; these parameters can include a center frequency ranging from 100 kHz-7M Hz; a pulse repetition rate of 50 micros-2 s on, 1 ms-10 s off; and a pressure at target area of 25 kPa-10 MPa. In various embodiments, the subject undergoing treatment may be monitored on a daily basis or every few days (e.g., every 2-3 days). Monitoring can include evaluating at improvements in clinical outcomes for the subject or evaluating improvements in the subject's blood markers, which may be performed by obtaining blood samples or using particular sensors. Parameters that can be evaluated include cytokines and other inflammatory or metabolic markers. The therapeutic beam of ultrasonic energy may be steered in different directions in order to provide therapeutic energy to different portions of the organ or to different organs (FIGS. 10A-10C). The steering of the beam enables the ability to stimulate a specific region of the organ continuously but also to stimulate different regions of an organ in a sequential manner, such as a few seconds or minutes in each location in order to stimulate multiple intended regions of the organ per therapy session. The steering of the beam also enables the ability to provide ultrasound energy between ribs or to avoid other structures that could be occluding the targeted organ region.

Therapeutic ultrasound may be delivered when the subject is at rest, e.g., while seated or lying down. When the subject is at rest, the subject's breathing rate is reduced and it is easier to track the location of the organ. For example, the spleen can more easily be tracked when the subject is at rest and breathing more slowly since the diaphragm (which the spleen is adjacent to) is moving more slowly and its movement changes direction less frequently. In addition to movements related to breathing, tracking the organ's location is more reliable when the subject is in the same position throughout the treatment period, since the organ may shift positions when the subject changes body posture and/or moves around. Thus, ultrasound stimulation may be stopped (or stimulation may not be started) when it is determined that the subject is actively moving (e.g., walking, running, or engaging in other ongoing movement) and/or has an elevated breathing rate, as determined by one or more biosensors associated with the subject's body.

Computer System

Figure 11:
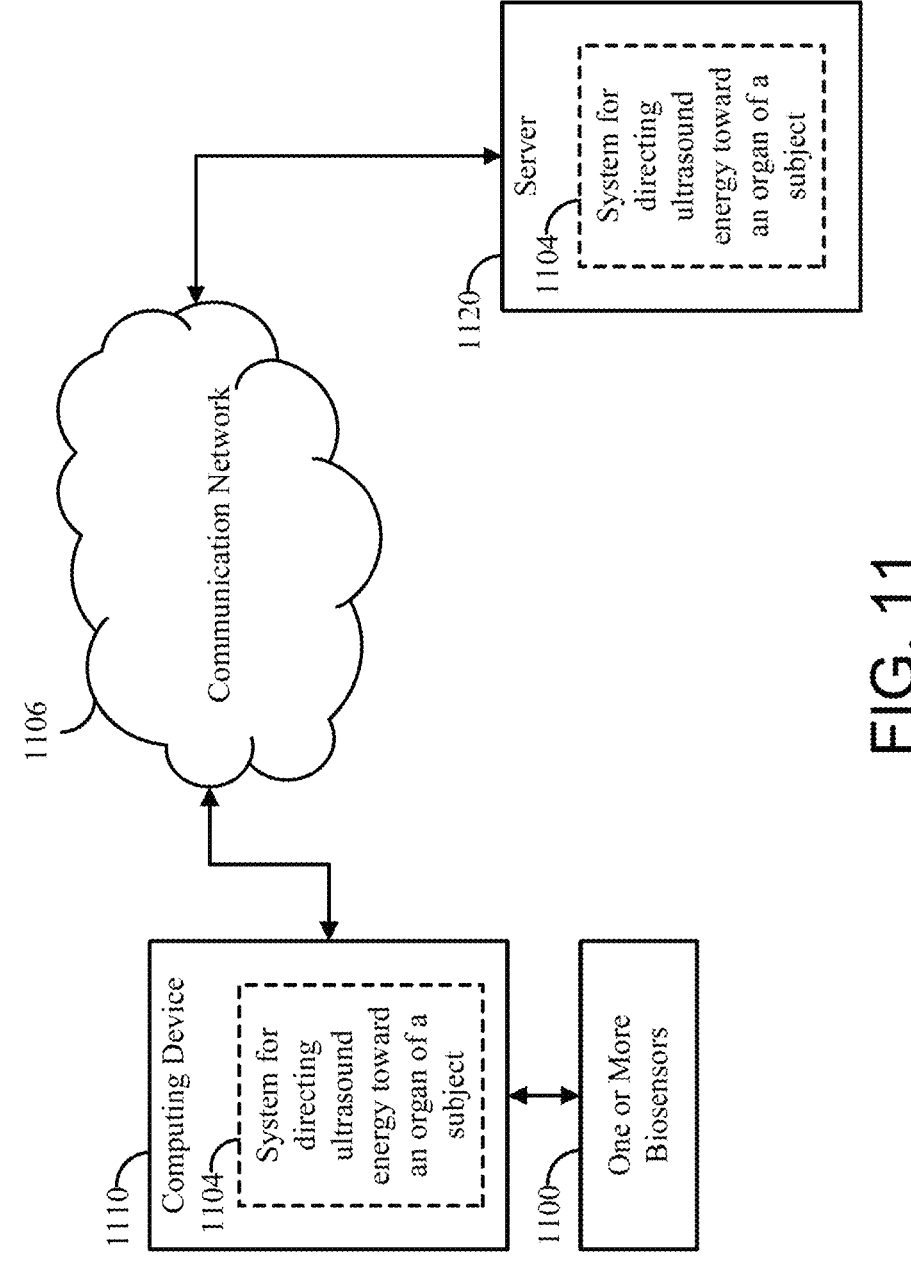
FIG. 11 shows an example of a system for directing ultrasound energy toward an organ of a subject in accordance with some embodiments of the disclosed subject matter.

Turning to FIG. 11, an example 1100 of a system (e.g., a data collection and processing system) for directing ultrasound energy toward an organ of a subject is shown in accordance with some embodiments of the disclosed subject matter. As shown in FIG. 11, a computing device 1110 can receive biosensor data from one or more biosensors 1100. In some embodiments, computing device 1110 can execute at least a portion of a system for directing ultrasound energy toward an organ of a subject 1104 to determine an organ location based on the biosensor data received from the one or more biosensors 1100. Additionally or alternatively, in some embodiments, computing device 1110 can communicate information about the biosensor data received from the one or more biosensors 1100 to a server 1120 over a communication network 1106, which can execute at least a portion of system for directing ultrasound energy toward an organ of a subject 1104 to determine the organ location or to stimulate the organ based on the biosensor data. In some such embodiments, server 1120 can return information to computing device 1110 (and/or any other suitable computing device) indicative of an output of system for directing ultrasound energy toward an organ of a subject 1104, such as the organ location information. In some embodiments, in addition to being used to direct ultrasonic energy, this information may be transmitted and/or presented to a user (e.g., a researcher, an operator, a clinician, etc.) and/or may be stored (e.g., as part of a research database or a medical record associated with a subject).

In some embodiments, computing device 1110 and/or server 1120 can be any suitable computing device or combination of devices, such as a desktop computer, a laptop computer, a smartphone, a tablet computer, a wearable computer, a server computer, a virtual machine being executed by a physical computing device, etc. As described herein, the system for directing ultrasound energy toward an organ of a subject 1104 can present information about the biosensor data, and/or the organ location information to a user (e.g., researcher and/or physician).

In some embodiments, communication network 1106 can be any suitable communication network or combination of communication networks. For example, communication network 1106 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some embodiments, communication network 1106 can be a local area network, a wide area network, a public network (e.g., the Internet), a private or semi-private network (e.g., a corporate or university intranet), any other suitable type of network, or any suitable combination of networks. Communications links shown in FIG. 11 can each be any suitable communications link or combination of communications links, such as wired links, fiber optic links, Wi-Fi links, Bluetooth links, cellular links, etc.

Figure 12:
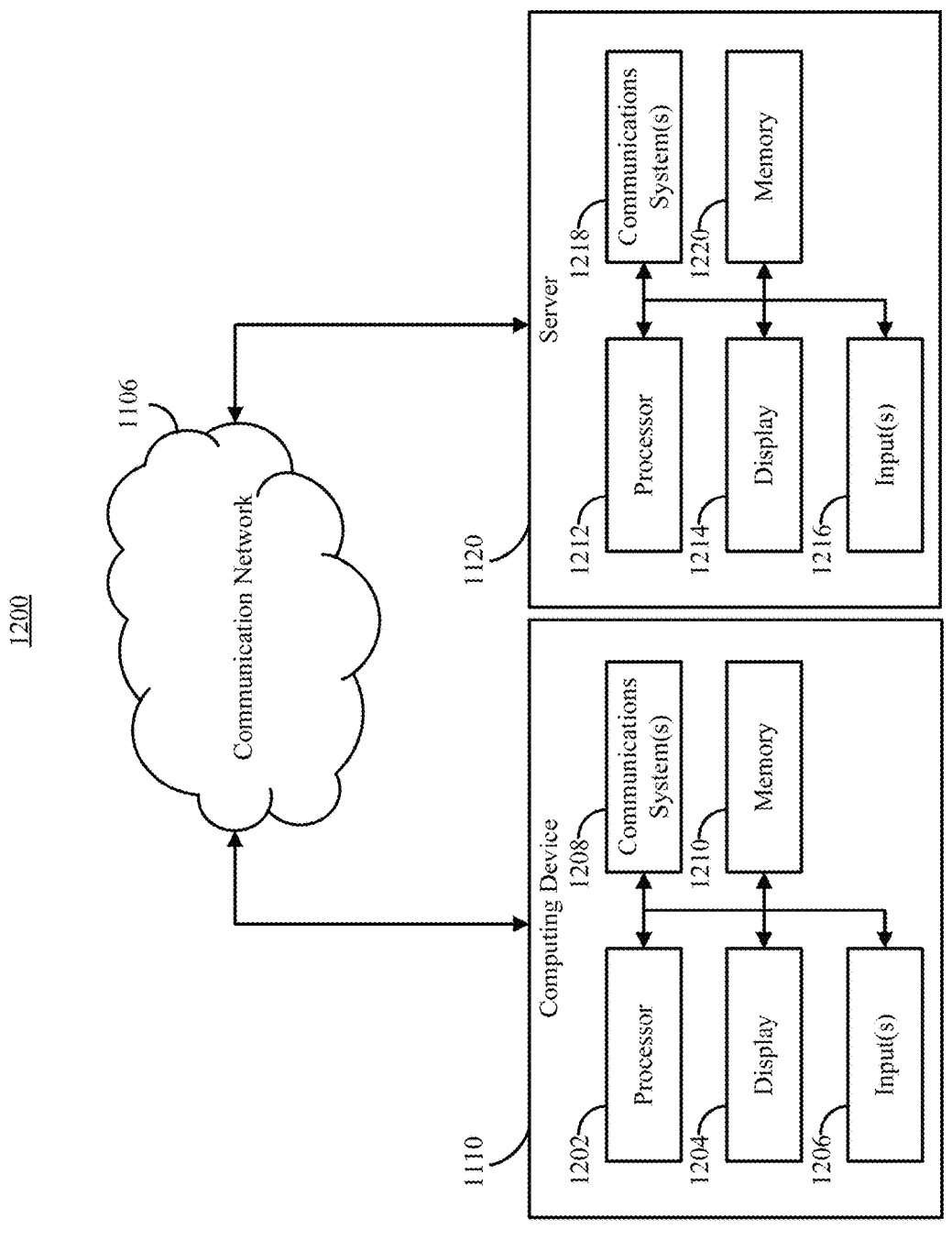
FIG. 12 shows an example of hardware that can be used to implement computing device and server in accordance with some embodiments of the disclosed subject matter.

FIG. 12 shows an example 1200 of hardware that can be used to implement computing device 1110 and server 1120 in accordance with some embodiments of the disclosed subject matter. As shown in FIG. 12, in some embodiments, computing device 1110 can include a processor 1202, a display 1204, one or more inputs 1206, one or more communication systems 1208, and/or memory 1210. In some embodiments, processor 1202 can be any suitable hardware processor or combination of processors, such as a central processing unit, a graphics processing unit, etc. In some embodiments, display 1204 can include any suitable display devices, such as a computer monitor, a touchscreen, a television, a smart watch, a smartphone, a tablet, etc. In some embodiments, inputs 1206 can include any suitable input devices and/or sensors that can be used to receive user input, such as a keyboard, a mouse, a touchscreen, a microphone, etc.

In some embodiments, communications systems 1208 can include any suitable hardware, firmware, and/or software for communicating information over communication network 1106 and/or any other suitable communication networks. For example, communications systems 1208 can include one or more transceivers, one or more communication chips and/or chip sets, etc. In a more particular example, communications systems 1208 can include hardware, firmware and/or software that can be used to establish a Wi-Fi connection, a Bluetooth connection, a cellular connection, an Ethernet connection, etc.

In some embodiments, memory 1210 can include any suitable storage device or devices that can be used to store instructions, values, etc., that can be used, for example, by processor 1202 to present content using display 1204, to communicate with server 1120 via communications system(s) 1208, etc. Memory 1210 can include any suitable volatile memory, non-volatile memory, storage, or any suitable combination thereof. For example, memory 1210 can include RAM, ROM, EEPROM, one or more flash drives, one or more hard disks, one or more solid state drives, one or more optical drives, etc. In some embodiments, memory 1210 can have encoded thereon a computer program for controlling operation of computing device 1110. In such embodiments, processor 1202 can execute at least a portion of the computer program to present content (e.g., images, user interfaces, graphics, tables, etc.), receive content from server 1120, transmit information to server 1120, etc.

In some embodiments, server 1120 can include a processor 1212, a display 1214, one or more inputs 1216, one or more communications systems 1218, and/or memory 1220. In some embodiments, processor 1212 can be any suitable hardware processor or combination of processors, such as a central processing unit, a graphics processing unit, etc. In some embodiments, display 1214 can include any suitable display devices, such as a computer monitor, a touchscreen, a television, a smart watch, a smartphone, a tablet, etc. In some embodiments, inputs 1216 can include any suitable input devices and/or sensors that can be used to receive user input, such as a keyboard, a mouse, a touchscreen, a microphone, etc.

In some embodiments, communications systems 1218 can include any suitable hardware, firmware, and/or software for communicating information over communication network 1106 and/or any other suitable communication networks. For example, communications systems 1218 can include one or more transceivers, one or more communication chips and/or chip sets, etc. In a more particular example, communications systems 1218 can include hardware, firmware and/or software that can be used to establish a Wi-Fi connection, a Bluetooth connection, a cellular connection, an Ethernet connection, etc.

In some embodiments, memory 1220 can include any suitable storage device or devices that can be used to store instructions, values, etc., that can be used, for example, by processor 1212 to present content using display 1214, to communicate with one or more computing devices 1110, etc. Memory 1220 can include any suitable volatile memory, non-volatile memory, storage, or any suitable combination thereof. For example, memory 1220 can include RAM, ROM, EEPROM, one or more flash drives, one or more hard disks, one or more solid state drives, one or more optical drives, etc. In some embodiments, memory 1220 can have encoded thereon a server program for controlling operation of server 1120. In such embodiments, processor 1212 can execute at least a portion of the server program to transmit information and/or content (e.g., results of a tissue identification and/or classification, a user interface, etc.) to one or more computing devices 1110, receive information and/or content from one or more computing devices 1110, receive instructions from one or more devices (e.g., a personal computer, a laptop computer, a tablet computer, a smartphone, etc.), etc.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EE- PROM), etc.), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

In some embodiments, the optical signals are detected by photodiodes. It should be recognized that any opto-electronic conversion device including but not limited to photo detectors, photodiodes, line-scan and two-dimensional cameras, and photodiode arrays can be used to perform this detection function.

It should be noted that, as used herein, the term mechanism can encompass hardware, software, firmware, or any suitable combination thereof.

Figure 13:
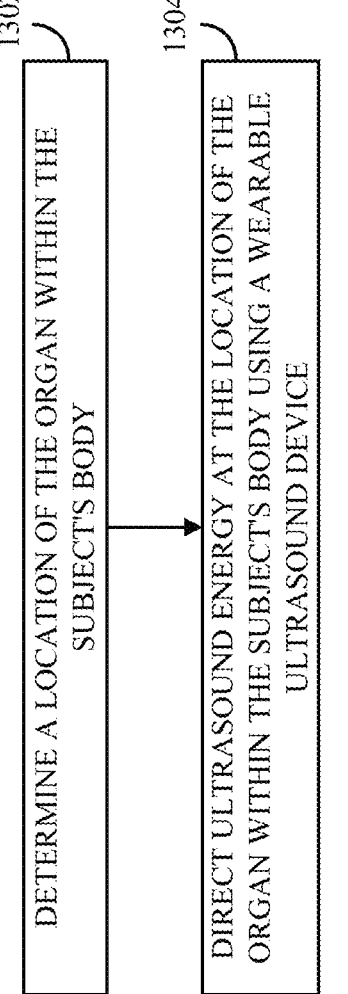
FIG. 13 shows an example of a process for directing ultrasound energy toward an organ of a subject in accordance with some embodiments of the disclosed subject matter.

FIG. 13 shows an example 1300 of a process for directing ultrasound energy toward an organ of a subject in accordance with some embodiments of the disclosed subject matter. As shown in FIG. 13, at 1302, process 1300 can determine a location of the organ within the subject's body. Finally, at 1304, process 1300 can direct ultrasound energy at the location of the organ within the subject's body using a wearable ultrasound device.

It should be understood that the above described steps of the process of FIG. 13 can be executed or performed in any order or sequence not limited to the order and sequence shown and described in the figures. Also, some of the above steps of the processes of FIG. 13 can be executed or performed substantially simultaneously where appropriate or in parallel to reduce latency and processing times.

EXAMPLES

The following are non-limiting examples of embodiments of the present procedures:

Example 1—Measuring Spleen Movement in Different Body Positions with Different Inspiration Depths The following Example demonstrates how the spleen location may be tracked in a subject using ultrasound imaging for a variety of body positions and breathing patterns of the subject. These types of measurements may be part of an initial fitting procedure that a subject may undergo in order to characterize the movements of the spleen under different conditions and correlate these movements with sensor information.

The right side of FIG. 14 shows a diagram of placement of an ultrasound transducer on a subject so that it is oriented along the space between the subject's ribs, such that the transducer is shown on a diagonal axis to the subject's left flank. As shown in the left side of FIG. 14, the ultrasound images from a transducer placed in this way are able to visualize different two-dimensional slices through the spleen while the subject is breathing, where the C-shaped dark area is a slice through the spleen. The symbol P in the ultrasound image on the left is also shown in the placement diagram on the right, providing information as to the orientation of the image relative to the subject's body. Ultrasound imaging videos were recorded while the subject was breathing, in various body positions including: sitting, supine, prone, and laying on the right side. To analyze motion, video screenshots during inhale and exhale were overlaid and the edge of the spleen was tracked between both overlays and the distance digitally measured. Multiple screenshots could also be stacked to create a three-dimensional rendering of the spleen shape, dimensions, location and movement within the body.

Figure 15:

FIG. 15 shows data collected as shown in FIG. 14 of the movement of the spleen associated with a heartbeat while the subject is at rest. The data shows that the spleen moves a relatively small amount under these conditions, 1.7 mm in this example.

Figure 16:

FIG. 16 shows data collected as shown in FIG. 14 of the movement of the spleen associated with breathing while the subject is at rest. The data shows that the spleen moves 11.1 mm during an inhale toward the hips under these conditions. In addition, it was determined that, while the subject was sitting (as in FIGS. 16 and 17), the distance to the spleen was 8.9 mm during exhale.

Figure 17:

FIG. 17 shows data collected as shown in FIG. 14 of the movement of the spleen associated with breathing a large breath while the subject is at rest. The data shows that the spleen moves 26.9 mm during a large inhale under these conditions. As noted above, it was determined that the distance to the spleen was 8.9 mm during exhale while the subject was in the sitting position.

Figure 18:

FIG. 18 shows data collected as shown in FIG. 14 of the movement of the spleen during normal at-rest breathing while lying on the right side. The data shows that the spleen moves 12.1 mm under these conditions, which is 9% greater movement than when the subject is in a sitting position. The distance to the spleen while lying on the side was determined to be 15.4 mm during exhale.

Figure 19:

FIG. 19 shows data collected as shown in FIG. 14 of the movement of the spleen during a large inhale while lying on the right side. The data shows that the spleen moves 22.9 mm during a large inhale under these conditions, which is 15% less movement than when the subject is in a sitting position during a large inhale. The distance to the spleen while lying on the side was determined to be 12.4 mm during exhale.

Figure 20:

FIG. 20 shows data collected as shown in FIG. 14 of the movement of the spleen during normal at-rest breathing while lying on the back (supine). The data shows that the spleen moves 18.9 mm under these conditions, which is 70% greater movement than when the subject is in a sitting position during normal at-rest breathing. The distance to the spleen while lying on the back was determined to be 11.6 mm during exhale.

Figure 21:

FIG. 21 shows data collected as shown in FIG. 14 of the movement of the spleen during a large inhale while lying on the back (supine). The data shows that the spleen moves 30.8 mm during a large inhale under these conditions, which is 14% greater movement than when the subject is in a sitting position during a large inhale. The distance to the spleen while lying on the back was determined to be 13.2 mm during exhale.

Figure 22:

FIG. 22 shows data collected as shown in FIG. 14 of the movement of the spleen during normal at-rest breathing while lying on the stomach (prone). The data shows that the spleen moves 8.8 mm during normal breathing under these conditions, which is 21% less movement than when the subject is in a sitting position during normal at-rest breathing. The distance to the spleen while lying on the stomach was determined to be 11.4 mm during exhale.

Figure 23:

FIG. 23 shows data collected as shown in FIG. 14 of the movement of the spleen during a large inhale while lying on the stomach (prone). The data shows that the spleen moves 21.1 mm during a large inhale under these conditions, which is 22% less movement than when the subject is in a sitting position during a large inhale. The distance to the spleen while lying on the stomach was determined to be 10.7 mm during exhale.

Figure 24:
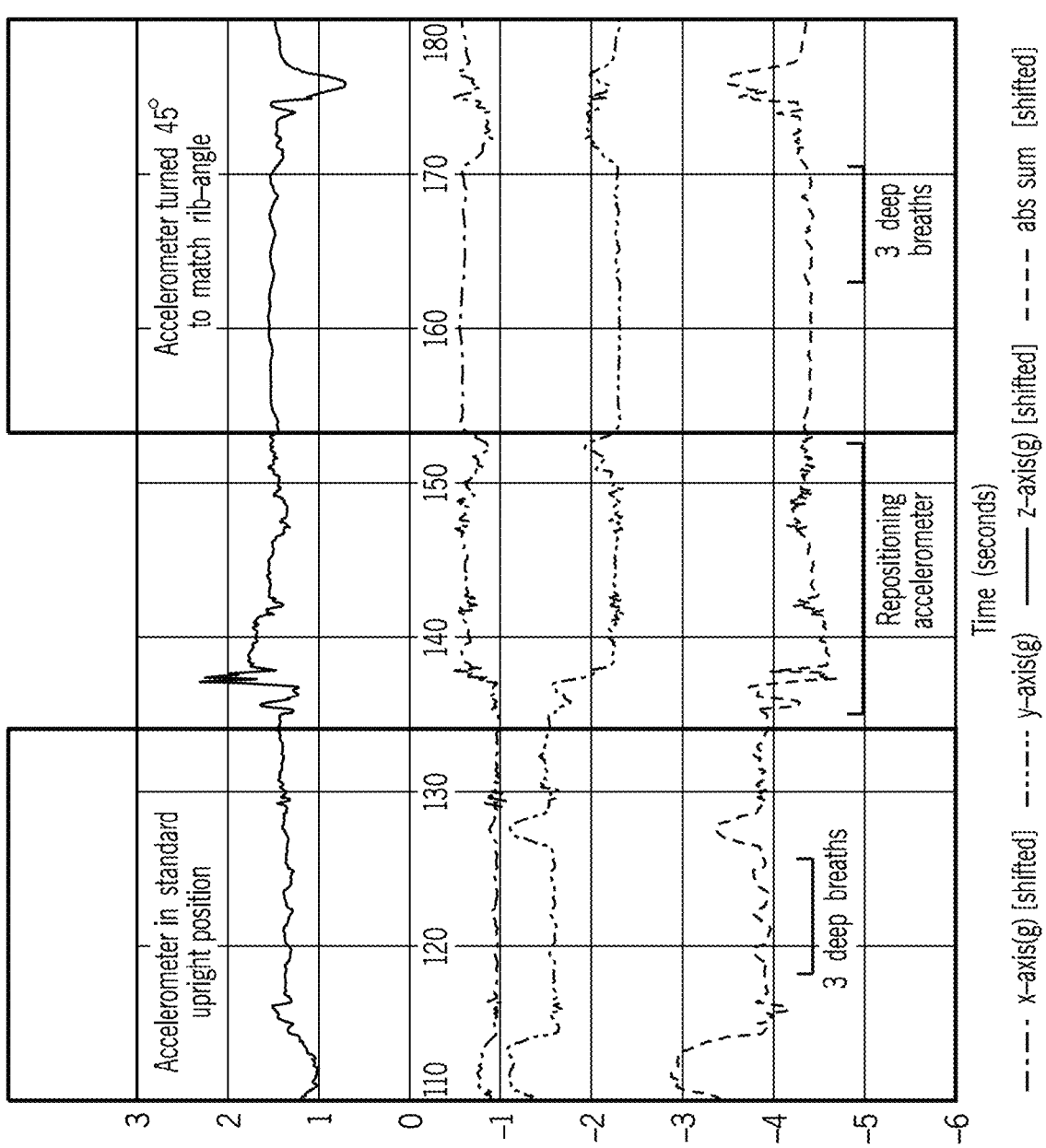

FIG. 24 shows data demonstrating that the accelerometer can detect breathing whether it is mounted in a standard vertical position or positioned at any angle. The left portion of FIG. 24 shows data obtained during three breaths when the accelerometer was attached to the subject in a standard upright position, where the top trace is the z-axis, the second trace is the x-axis, the third trace is the y-axis, and the bottom trace is the absolute sum; the bottom three traces have been shifted in order to improve visibility of the data. The center portion of FIG. 24 shows data obtained during a transition when the accelerometer was rotated 45°. The right portion of FIG. 24 shows data obtained during three breaths when the accelerometer was attached to the subject at a 45° angle to match the rib angle (see FIG. 14). As shown in the bottom trace (the absolute sum), the data show that the accelerometer was able to detect three deep breaths in either orientation (indicated by a bracket under the data corresponding to the three breaths).

Figure 25:
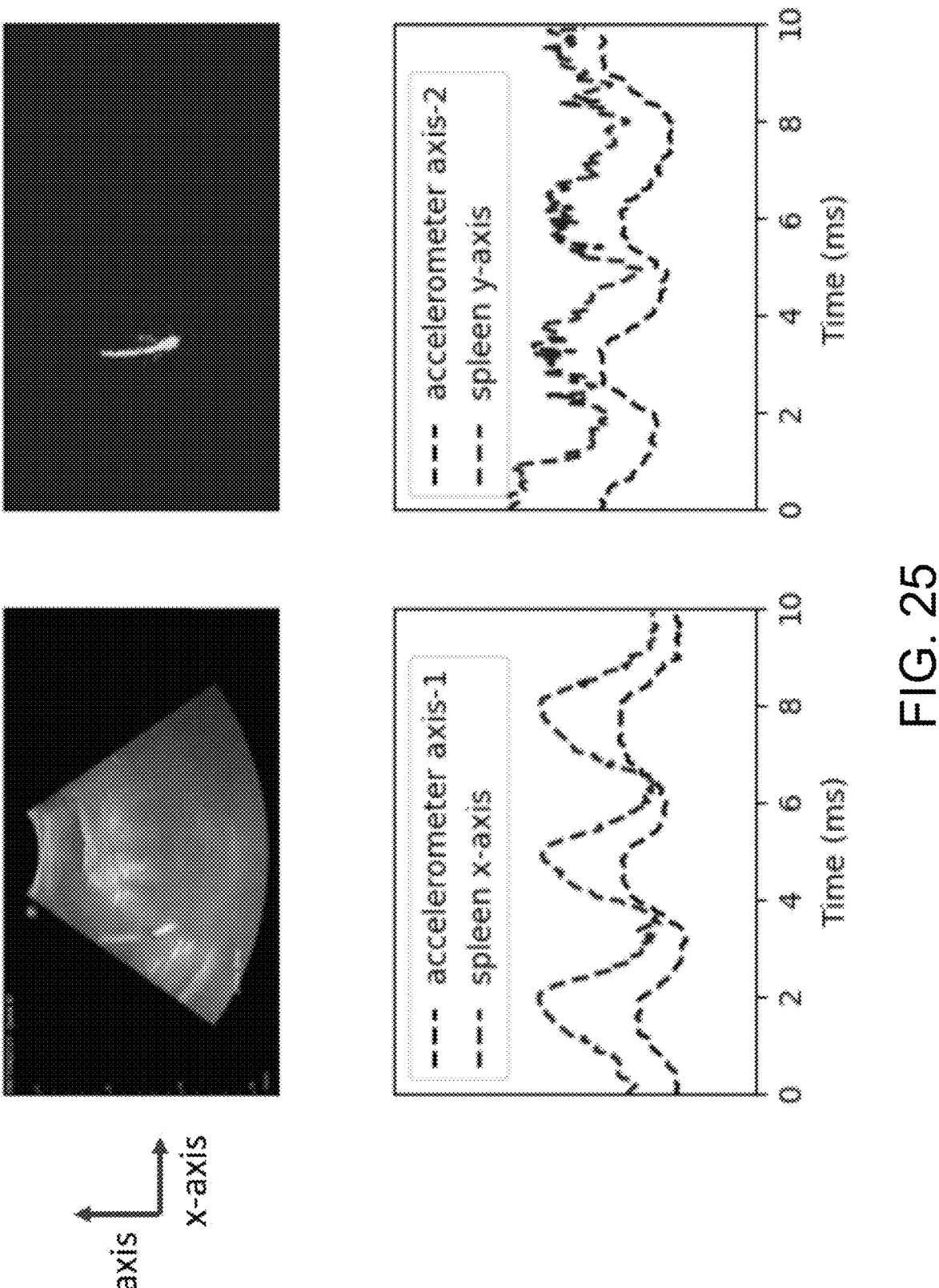
FIG. 25 shows data demonstrating that the accelerometer signals relating to different orientations/positions can track or predict the motion of the spleen in different directions in three-dimensional space (i.e. x, y, and z axes).

FIG. 25 shows data demonstrating that the accelerometer signals relating to different orientations/positions can track or predict the motion of the spleen in different directions in three-dimensional space (i.e., x, y, and z axes). When accelerometry is recorded in 3 or more axes, the data predicts the three-dimensional spleen motion. The top two panels show an ultrasound image of the abdominal region including the spleen (left) as well as an analysis of the spleen motion (right) from a sequence of such images. The bottom two panels show movement of the spleen in the x- and y-axes as determined from the image sequence compared to movements determined from two different accelerometer axes. These results show that accelerometer data can be used to track the location and motion of the spleen in all directions in a reliable and accurate manner.

The examples described above demonstrate that spleen position can be tracked during breathing and differences in the type of breathing (at-rest, large inhale) and body position (sitting, lying on the side, lying on the back, lying on the front) can be measured and accounted for, and that breathing can be tracked using accelerometers independent of the orientation of the accelerometer on the subject's body.

Example 2—Fitting of a Wearable Device

A subject will undergo an extensive procedure for fitting the wearable ultrasonic therapy device. The procedure will collect sufficient data to allow the device to track the location of the spleen during the subject's normal activities for the purpose of delivering ultrasonic therapy while the subject wears the device.

The information will include physical, biophysical and demographic information (age, sex, race, height, weight, rib spacings, circumference of chest, circumference of waist, dimensions of organ, distances of organ to body surface, heart rates, breathing rates, breathing volumes, pre-existing conditions or disease state, etc.) and will also include a baseline abdominal ultrasound imaging and ultrasound video recording session (e.g., using a commercial ultrasound imaging device and/or a wearable ultrasound device) which will be conducted to determine spleen location, depth, and respiratory motion of the spleen in various body positions (e.g., sitting, lying prone, moving (e.g., shifting orientation), etc.) and various breathing volumes as shown in Example 1. During the video recording session, biosensor data will be collected from one or more of a wearable ultrasound device, an accelerometer, a pulse oximeter, a respirometer, an EKG electrode, an EMG electrode, a wearable fitness device, or other biosensor associated with the subject's body. The fitting session will take at least one hour and possibly up to three hours.

The subject's skin will be marked (e.g., using henna, permanent ink markers, or other durable marking materials or procedures) over the spleen to indicate the location where the wearable ultrasound-therapy device will be placed during the treatment phase.

Based on the information obtained during the fitting procedure, the movements of the subject's organ (e.g., spleen) under various conditions will be identified and characterized and correlated with the biosensor data.

The subject's physical, biophysical and demographic information will be added to a database along with the baseline abdominal imaging and video recording session information and biosensor data. This database will then be used to facilitate fitting of other subjects based on matching, extrapolation, and other processing of the data in the database in comparison to the data of a new subject.

Example 3—Fitting of a Wearable Device Using Database Information

A subject will be fitted with a wearable ultrasonic device in a shortened fitting session which will take less than twenty minutes. The fitting session will be shortened by using information in a database obtained from other subjects' fittings which provides information about typical amounts of movement of the organ associated with different body positions and movement states. The database will use physical, biophysical and demographic information from the subject to query the database to obtain information regarding correlations between biosensor information and organ movement. The subject will undergo limited noninvasive imaging to identify the organ of interest (e.g., the spleen) to help determine the placement of the wearable device. The subject's skin will be marked (e.g., using henna, permanent ink markers, or other durable marking materials or procedures) over the spleen to indicate the location where the wearable ultrasound-therapy device will be placed during the treatment phase.

The wearable device will be programmed in a manner that is specific to the subject to direct ultrasound energy towards the organ of interest based on information received from biosensors, e.g., accelerometers. The programming will provide correlations between biosensor readings and organ locations as determined during fitting by direct imaging of the organ and/or information obtained from a database of information from previously-fitted subjects.

Example 4—Ultrasonic Treatment with a Wearable Device

The subject will attach the wearable device near the organ of interest (e.g., the spleen) using the skin markings that are applied during the fitting as a guide for placement. The subject will activate the device to implement a detection and treatment program that is based on input received from biosensors, particularly accelerometers, associated with the subject's body. The subject will go about their normal activities and the wearable device (sometimes in conjunction with an external device) will determine when to apply therapeutic ultrasound to the subject's organ. The wearable device will preferentially apply therapy when it is determined that the subject is breathing slowly and/or at rest (e.g., seated). The wearable device will apply the therapeutic ultrasound for at least 9 minutes while the subject is at rest. Prior to and during therapeutic treatment the wearable device will perform a rib detection procedure to identify the location of the rib(s) in order to determine which portion(s) of the ultrasonic transducer to use and/or the beam steering patterns to use to stimulate the organ. The wearable device will also perform direct measurements of the location of the organ based on procedures including ultrasound-resolved border detection, volumetric ultrasonic imaging, and ultrasound-based elasticity/elastography measurements of the organ.

Thus, while the invention has been described above in connection with particular embodiments and examples, the invention is not necessarily so limited, and that numerous other embodiments, examples, uses, modifications and departures from the embodiments, examples and uses are intended to be encompassed by the claims attached hereto.

What is claimed is:

1. A system for directing ultrasound energy toward an organ of a subject, comprising:
    a processor configured to:
        obtain real-time biosensor data from a biosensor associated with a subject's body, the biosensor comprising an accelerometer; and
        determine a predicted location of an organ within the subject's body based on the real-time accelerometer biosensor data and a correlation between accelerometer biosensor data and information identifying measured locations of the organ; and
    a wearable ultrasound device configured to direct ultrasound energy at the predicted location of the organ within the subject's body.

2. The system of claim 1, wherein the processor is further configured to determine the correlation between the accelerometer biosensor data and the measured locations of the organ within the subject's body.

3. The system of claim 1, wherein the processor, when determining a predicted location of an organ within the subject's body based on the real-time accelerometer biosensor data and the correlation between accelerometer biosensor data and the information identifying measured locations of the organ, is further configured to:
    determine the predicted location of an organ within the subject's body based on the real-time accelerometer biosensor data and the correlation between the accelerometer biosensor data and the information identifying measured locations of the organ for a plurality of subjects based on correlation data in a database.

4. The system of claim 3, wherein the processor, when obtaining real-time biosensor data from a biosensor associated with the subject's body, is further configured to:
    obtain further real-time biosensor data from at least one of a pulse oximeter, a respirometer, an EMG electrode, or an EKG electrode associated with the subject's body.

5. The system of claim 4, wherein the processor, when determining the predicted location of the organ within the subject's body based on the real-time accelerometer biosensor data and the correlation between the accelerometer biosensor data and the information identifying measured locations of the organ, is further configured to:
    determine, based on the real-time biosensor data, whether the subject's body is standing, sitting, moving, or lying.

6. The system of claim 5, wherein the processor, when determining a predicted location of the organ within the subject's body based on the real-time accelerometer biosensor data and the correlation between the accelerometer biosensor data and the information identifying measured locations of the organ, is further configured to:
    determine the subject's breathing status based on the real-time accelerometer biosensor data; and
    determine the predicted location of the organ within the subject's body based on the subject's breathing status.

7. The system of claim 6, wherein the processor, when obtaining the real-time biosensor data from the biosensor associated with the subject's body, is further configured to:
    obtain the real-time biosensor data from a respirometer associated with the subject's body.

8. The system of claim 6, wherein the processor, when determining the subject's breathing status based on the real-time accelerometer biosensor data, is further configured to:
    determine, based on the real-time accelerometer biosensor data, whether the subject's breathing status is breathing quickly or breathing slowly.

9. The system of claim 8, wherein the wearable ultrasound device, when directing ultrasound energy at the predicted location of the organ within the subject's body, is further configured to:
    direct ultrasound energy at the predicted location of the organ within the subject's body based on determining that the subject's body position is sitting and that the subject's breathing status is breathing slowly.

10. The system of claim 9, wherein the wearable ultrasound device, when directing ultrasound energy at the predicted location of the organ within the subject's body, is further configured to:
    direct ultrasound energy at the location of the organ within the subject's body for at least nine minutes.

11. The system of claim 1, wherein the wearable ultrasound device, when determining the location of the organ within the subject's body using the wearable ultrasound device, is further configured to:
    detect a location of a rib within the subject's body using the wearable ultrasound device,
    adjust an output of the wearable ultrasound device to avoid the location of the rib within the subject's body, and
    direct ultrasound energy at the organ within the subject's body based on the adjusted output of the wearable ultrasound device.

12. The system of claim 1, wherein the wearable ultrasound device, when determining a location of the organ within the subject's body, is further configured to:
    determine a location of the organ within the subject's body based on elastography measurements of the organ using the wearable device.

13. The system of claim 1, wherein the wearable ultrasound device, when determining a location of the organ within the subject's body, is further configured to:
    determine a location of the organ within the subject's body based on ultrasound-resolved border detection of the organ using the wearable device.

14. The system of claim 1, wherein the wearable ultrasound device, when determining a location of the organ within the subject's body, is further configured to:
    determine a location of the organ within the subject's body based on ultrasound detection of at least one of a blood vessel or a nerve associated with the organ using the wearable device.

15. The system of claim 1, wherein the wearable ultrasound device, when determining the location of the organ within the subject's body, is further configured to:

determine, for each of a plurality of positions of the subject's body, the location of the organ within the subject's body using a non-invasive imaging modality, collect, for each of the plurality of positions of the subject's body, initial biosensor data from at least one of the wearable ultrasound device, an accelerometer, a pulse oximeter, a respirometer, an EMG electrode, or an EKG electrode associated with the subject's body, and generate, for each of the plurality of positions of the subject's body, correlations of the location of the organ within the subject's body with the initial biosensor data.

16. The system of claim 15, wherein the wearable ultrasound device, when determining the location of the organ within the subject's body, is further configured to:

store the correlations of the location of the organ within the subject's body with the initial biosensor data in a database.

17. The system of claim 16, wherein the wearable ultrasound device, when determining a location of the organ within the subject's body during movement of the subject, is further configured to:

collect additional biosensor data from at least one of the wearable ultrasound device, the accelerometer, the pulse oximeter, the respirometer, the EMG electrode, or the EKG electrode associated with the subject's body, determine the location of the organ within the subject's body based on the additional biosensor data and the correlations stored in the database, and direct ultrasound energy at the organ within the subject's body based on the determined location.

18. The system of claim 1, wherein the organ is a spleen.

19. The system of claim 1, wherein the information identifying measured locations of the organ comprises a database.

* * * * *